United States Patent
Shimada et al.

(10) Patent No.: US 6,844,444 B2
(45) Date of Patent: Jan. 18, 2005

(54) 1H-1,2,4-TRIAZOLE-5-YL-ACETIC ESTER COMPOUND

(75) Inventors: Yasuhiro Shimada, Minami-ashigara (JP); Hideki Maeta, Minami-ashigara (JP); Yoshio Shimura, Minami-ashigara (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/061,249

(22) Filed: Feb. 4, 2002

(65) Prior Publication Data

US 2002/0107399 A1 Aug. 8, 2002

Related U.S. Application Data

(62) Division of application No. 09/003,881, filed on Jan. 7, 1998, now Pat. No. 6,384,219.

(30) Foreign Application Priority Data

Jan. 13, 1997 (JP) ........................... 14823/1997
Jan. 13, 1997 (JP) ........................... 14824/1997

(51) Int. Cl.[7] ........................... C07D 249/08

(52) U.S. Cl. ................... 548/268.6; 548/269.4

(58) Field of Search ................ 548/268.6, 269.4

(56) References Cited

U.S. PATENT DOCUMENTS 5,756,274 A    5/1998  Matsuda et al.

FOREIGN PATENT DOCUMENTS

EP    714892 A1    6/1996

OTHER PUBLICATIONS

Shimada et al, "Silver Halide Color, etc" CA 127:197689 (1997).*
Makuta, T., Chemical Abstracts, vol. 127, No. 72946 (1997).
Shimada, Y. et al., Chemical Abstracts, vol. 127, No. 197689 (1997).

* cited by examiner

*Primary Examiner*—Patricia L. Morris
(74) *Attorney, Agent, or Firm*—Birch, Stewart, Kolasch & Birch, LLP.

(57) ABSTRACT

There is disclosed a 1H-pyrrole-[1,2-b][1,2,4]triazole compound represented by formula (I):

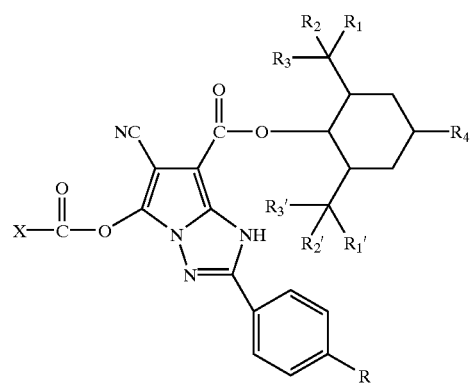

formula (I)

wherein R is an alkyl group; $R_1$, $R_2$, $R_3$, $R_1'$, $R_2'$, and $R_3'$ each are a hydrogen atom or an alkyl group; $R_1$ and $R_2$, and $R_1'$ and $R_2'$ may bond together to form a ring, respectively; $R_4$ is a hydrogen atom or an alkyl group, and X is heterocyclic group, a substituted amino group, or an aryl group. The compound is useful as a photographic cyan coupler. There is also disclosed synthetic intermediates of the compound and a production method of the intermediates.

5 Claims, No Drawings

1H-1,2,4-TRIAZOLE-5-YL-ACETIC ESTER COMPOUND

This application is a divisional of application Ser. No. 09/003,881, filed on Jan. 7, 1998, now U.S. Pat. No. 6,384,219, the entire contents of which are hereby incorporated by reference and for which priority is claimed under 35 U.S.C. §120; and this application claims priority of application Ser. No. 9-14823 and 9-14824 filed in Japan on Jan. 13, 1997 under 35 U.S.C. §119.

FIELD OF THE INVENTION

The present invention relates to a novel 1H-pyrrole-[1,2-b][1,2,4]triazole compound useful as a synthetic intermediate of physiological active substances, including medicines, agricultural chemicals, and the like, as a photographic cyan coupler, as a dye for heat transfer dye-donative materials, and as a precursor of a filter dye for solid state television camera tubes and color liquid crystal televisions. The present invention also relates to a 1H-1,2,4-triazole compound that is an intermediate for synthesizing the same efficiently.

Further, the present invention relates to a method for synthesizing cyclohexyl acetates useful, for example, as synthetic intermediates of dyes and as synthetic intermediates of dye-forming couplers, in the field of photographic chemistry.

BACKGROUND OF THE INVENTION 1H-pyrrole-[1,2-b][1,2,4]triazole derivatives are described, with respect to their reactivities, generally, in Ukrainski Khimicheskii Zhurnal, Vol. 41, No. 2, pages 181 to 185 (1975), and in Khimiya Geterotsiklicheskikh Scedine nii, No. 2, pages 261 to 267 (1974), and their use as medicines and the like is described in U.S. Pat. No. 4,358,457 and U.S. Pat. No. 4,962,202. Further, the derivatives are described as photographic magenta couplers and magenta dyes in Nihon Shashin Gakkai Showa 60-Nendo Nenji Taikai Koen Yoshi-shu, JP-A-62-278552 ("JP-A" means unexamined published Japanese patent application), JP-A-62-279339, JP-A-1-288835, U.S. Pat. No. 4,910,127 and EP-A-491 197.

Furthermore, U.S. Pat. Nos. 5,256,526, 5,384,236, and 5,547,826 disclose that 1H-pyrrole-[1,2-b][1,2,4]triazole derivatives can be made into compounds useful as photographic cyan couplers by introducing electron-attracting groups to the 6-position and the 7-position of the 1H-pyrrole-[1,2-b][1,2,4]triazole derivatives. As methods for synthesizing 1H-pyrrole-[1,2-b][1,2,4)triazole derivatives having electron-attracting groups at the 6-position and the 7-position, synthetic methods wherein 1H-1,2,4-triazole derivatives are used as a starting material are described in JP-A-5-202,004 and JP-A-5-255333. In addition, JP-A-7-48376 and JP-A-8-109172 disclose compounds useful as photographic cyan couplers and methods for synthesizing them, and also their efficient synthetic methods.

On the other hand, many general esterification methods that use condensation of carboxylic acids with alcohols are known, and examples are described in detail in Jikken Kagaku-koza, Vol. 22 (Maruzen, 1992), pp. 43 to 83. Among these, for example, a method for synthesizing an ester by using an equilibrium reaction in the presence of an acid catalyst under dehydration conditions, or a method for synthesizing an ester by using a condensing agent, such as dicyclohexylcarbodiimide and ethyl azodicarboxylate, are often used. Furthermore, there is an acid chloride method for synthesizing an ester, wherein a carboxylic acid is converted by means of thionyl chloride, phosphorus trichloride, or oxalyl chloride, to an acid chloride, and the acid chloride is subjected to addition reaction of an alcohol, in the presence of a base.

The foregoing general esterification methods, however, could not be applied to the synthesis of ester compounds represented by the below-shown formula (IX) using carboxylic acids represented by the below-shown formula (VII) and cyclohexanols represented by the below-shown formula (VI), which are intended to be condensed in the present invention. Namely, the method that uses acid catalysts is accompanied by the problem that large amounts of cyclohexanols are used, and the method that uses condensing agents and the acid chloride method can hardly give the intended ester compounds, because, in the esterification of cyclohexanols, carboxylic acid components are preferentially decomposed. Only one method, using trifluoroacetic anhydride (($CF_3CO)_2O$), described in Journal of Organic Chemistry, Vol. 30, page 927 (1965), has been applied, but the reagent is expensive and the treatment of the waste liquid is complicated, making the method difficult for use as an industrial process.

SUMMARY OF THE INVENTION

Therefore, a first object of the present invention is to provide a compound represented by the below-shown formula (I) useful as a photographic cyan coupler.

A second object of the present invention is to provide a synthetic intermediate(s) necessary for the synthesis of the compound represented by formula (I).

A third object of the present invention is to provide an industrial production method for obtaining cyclohexyl acetates represented by the below-shown formula (IX), in a good yield, by reacting cyclohexanols with carboxylic acids under mild reaction conditions.

Other and further objects, features, and advantages of the invention will appear more fully from the following description.

DETAILED DESCRIPTION OF THE INVENTION

The inventors of the present invention have studied intensively in various ways to develop 1H-pyrrole-(1,2-b][1,2,4] triazole compounds useful as photographic cyan couplers. The inventors have found that compounds wherein specific substituents are introduced to the 2-position and the 5-position of the pyrrolotriazole skeleton show excellent properties as photographic couplers in view of the hue of the dye formed, the coupling activity, the stain during and after photographic processing, the storage stability of them as couplers, the fastness of their dyes, etc., leading to the completion of the present invention.

The above objects have been attained by providing the compounds represented by the following formulas and the production method.

(1) A 1H-pyrrole-[1,2-b][1,2,4]triazole compound represented by formula (I):

formula (I)

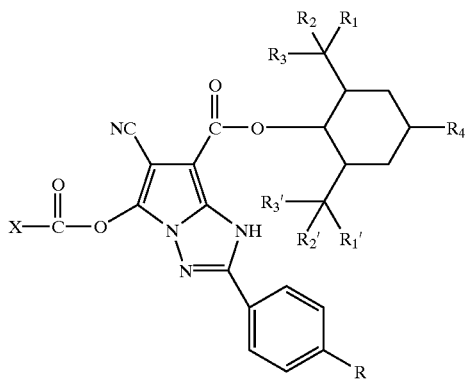

wherein, in formula (I), R represents an alkyl group; $R_1$, $R_2$, $R_3$, $R_1'$, $R_2'$, and $R_3'$ each represent a hydrogen atom or an alkyl group; $R_1$ and $R_2$, and $R_1'$ and $R_2'$, may bond together to form a ring, respectively; $R_4$ represents a hydrogen atom or an alkyl group, and X represents a heterocyclic group, a substituted amino group, or an aryl group.

(2) A 1H-1,2,4-triazole compound represented by formula (II):

formula (II)

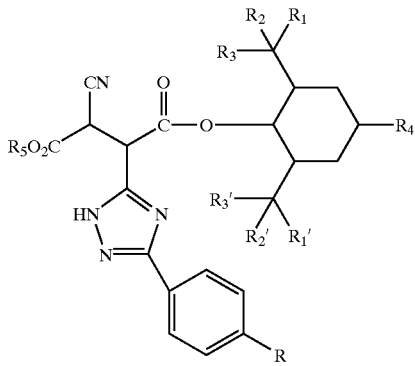

wherein, in formula (II), R represents an alkyl group; $R_1$, $R_2$, $R_3$, $R_1'$, $R_2'$, and $R_3'$ each represent a hydrogen atom or an alkyl group; $R_1$ and $R_2$, and $R_1'$ and $R_2'$, may bond together to form a ring, respectively; $R_4$ represents a hydrogen atom or an alkyl group, and $R_5$ represents a hydrogen atom or an alkyl group.

(3) A 1H-1,2,4-triazole compound represented by formula (III):

formula (III)

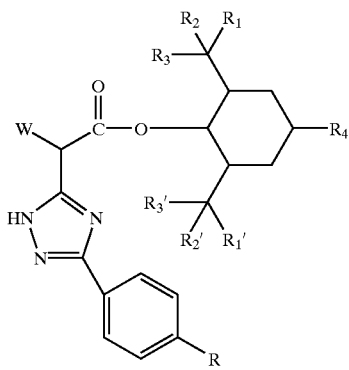

wherein, in formula (III), R represents an alkyl group; $R_1$, $R_2$, $R_3$, $R_1'$, $R_2'$, and $R_3'$ each represent a hydrogen atom or an alkyl group; $R_1$ and $R_2$, and $R_1'$ and $R_2'$, may bond together to form a ring, respectively; $R_4$ represents a hydrogen atom or an alkyl group, and W represents a halogen atom.

(4) A method for producing an ester compound represented by the following formula (IX), by reacting cyclohexanols represented by the following formula (VI) and carboxylic acids represented by the following formula (VII), using a carboxylic acid anhydride represented by the following formula (VIII):

formula (VI)

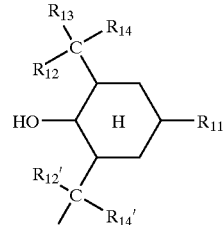

formula (VII)

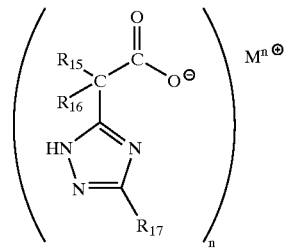

formula (VIII)

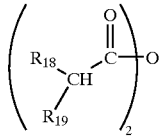

formula (IX)

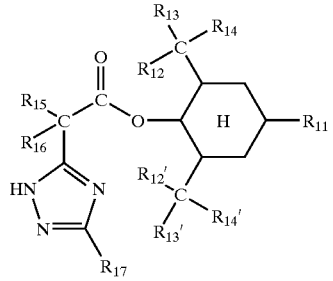

wherein $R_{11}$ represents a hydrogen atom or an alkyl group; $R_{12}$, $R_{13}$, $R_{14}$, $R_{12}'$, $R_{13}'$, and $R_{14}'$, which are the same or different, each represent a hydrogen atom or an alkyl group, $R_{12}$ and $R_{13}$, and $R_{12}'$ and $R_{13}'$ may bond together to a form ring, respectively; $R_{15}$ and $R_{16}$, which are the same or different, each represent a hydrogen atom, a halogen atom, an alkyl group, or an aryl group, with at least one of $R_{15}$ and $R_{16}$ being a hydrogen atom; $R_{17}$ represents an aliphatic group or an aryl group; $R_{18}$ and $R_{19}$, which are the same or different, each represent a hydrogen atom, a halogen atom, an alkyl group, or an aryl group; $R_{18}$ and $R_{19}$ may bond together to form a ring; M represents a hydrogen atom, an alkali metal, or an alkali earth metal; and n is an integer of 1 or 2.

(5) The method of producing an ester compound as stated in the above (4), wherein the reaction is carried out in the presence of a base.

(6) The method of producing an ester compound as stated in the above (4) or (5), wherein the carboxylic acid anhydride represented by formula (VIII) is an acetic anhydride.

(7) The method of producing an ester compound as stated in the above (4), (5), or (6), wherein the compound represented by formula (IX) is a 3-(4-t-butylphenyl)-1H-1,2,4-triazol-5-yl-acetic acid ester compound represented by the following formula:

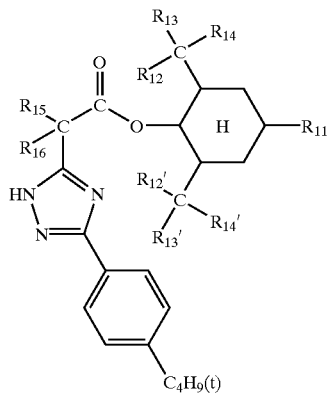

wherein $R_{11}$, $R_{12}$, $R_{13}$, $R_{14}$, $R_{12}'$, $R_{13}'$, $R_{14}'$, $R_{15}$, and $R_{16}$ each have the same meanings as defined above.

(8) The method for producing an ester compound as stated in the above (4), (5), (6), or (7), wherein the compound represented by formula (IX) is a 3-(4-t-butylphenyl)-1H-1,2,4-triazol-5-yl-acetic acid ester compound represented by the following formula:

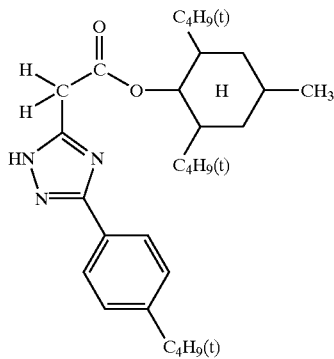

Herein, in the present invention, a group on the compound includes both a group having a substituent thereon and a group having no substituent (i.e. an unsubstituted group), unless otherwise specified.

Hereinbelow, the present invention is described in detail.

In formulae (I) to (III), R represents a straight-chain or branched-chain alkyl group having 1 to 12 carbon atoms, or a cyclic alkyl group (preferably having 3 to 8 carbon atoms), and preferably a straight-chain or branched-chain alkyl group having 1 to 8 carbon atoms, and more preferably a branched-chain alkyl group having 4 to 8 carbon atoms. Particularly preferably the alkyl group is a t-butyl group.

In formulae (I) to (III), $R_1$, $R_2$, $R_3$, $R_1'$, $R_2'$, and $R_3'$, which may be the same or different, each represent a hydrogen atom, or a straight-chain or branched-chain alkyl group having 1 to 24 carbon atoms, or a cyclic alkyl group (preferably having 3 to 8 carbon atoms). Preferably $R_1$, $R_2$, $R_3$, $R_1'$, $R_2'$, and $R_3'$ each represent a straight-chain or branched-chain alkyl group having 1 to 12 carbon atoms, or a cyclic alkyl group (preferably having 3 to 8 carbon atoms), and more preferably a straight-chain or branched-chain alkyl group having 1 to 6 carbon atoms, or a cyclic alkyl group (preferably having 3 to 8 carbon atoms), such as methyl, ethyl, propyl, and cyclohexyl. $R_1$ and $R_2$, and $R_1'$ and $R_2'$, may bond together to form a ring, respectively, and, for example, preferably $R_1$ and $R_2$, and $R_1'$ and $R_2'$, form, respectively, a lower alkylene group having 1 to 12 carbon atoms, and preferably they form methylene, ethylene, propylene, butylene, pentylene, or hexylene. A particularly preferable group represented by each of $R_1$, $R_2$, $R_3$, $R_1'$, $R_2'$, and $R_3'$ is a methyl group.

In formulae (I) to (III), $R_4$ represents a hydrogen group, or a straight-chain or branched-chain alkyl group having 1 to 36 carbon atoms, or a cyclic alkyl group (preferably having 3 to 8 carbon atoms), preferably a straight-chain or branched-chain alkyl group having 1 to 24 carbon atoms, and further preferably 1 to 12 carbon atoms, or cyclic alkyl group (preferably having 3 to 8 carbon atoms), and still further preferably a straight-chain or branched-chain alkyl group having 1 to 4 carbon atoms, such as methyl, ethyl, propyl, isopropyl, isobutyl, t-butyl, octyl, octadecyl, and cyclohexyl. A particularly preferable alkyl group is a methyl group.

In formula (II), $R_5$ represents a hydrogen atom or a straight-chain or branched-chain alkyl group having 1 to 4 carbon atoms, and preferably a straight-chain alkyl group having 1 to 2 carbon atoms. A particularly preferable alkyl group is a methyl group.

In formula (III), W represents a halogen atom, preferably a chlorine atom, a bromine atom, or an iodine atom, and particularly preferably a bromine atom.

In formula (I), X represents a heterocyclic group, a substituted amino group, or an aryl group. The heterocyclic ring is preferably a 5- to 8-membered ring having a nitrogen atom, an oxygen atom, or a sulfur atom, and the ring includes 1 to 36 carbon atoms (preferably 1 to 8 carbon atoms) in all, including the carbon atoms in the substituent, if any, and more preferably the heterocyclic ring is a 5- or 6-membered ring bonded through the nitrogen atom, with particular preference given to a 6-membered ring.

Specific examples of X include imidazole, pyrazole, triazole, lactam compounds, piperidine, pyrrolidine, pyrrole, morpholine, pyrazolidine, thiazolidino, and pyrazoline. Preferably X represents morpholine and piperidine, with particular preference given to morpholine.

As the substituent on the substituted-amino group, an aliphatic group, an aryl group, or a heterocyclic group can be mentioned. The aliphatic group includes a straight-chain or branched-chain alkyl group having 1 to 12 carbon atoms, or a cyclic alkyl group (preferably having 3 to 8 carbon atoms), and preferably a straight-chain alkyl group having 1 to 8 carbon atoms, each of which may be substituted by a cyano group, an alkoxy group (e.g. methoxy), an alkoxycarbonyl group, chlorine, a hydroxyl group, a carboxyl group, or the like. As the substituted amino group, a di-substituted amino group is preferred to a mono-substituted amino group.

Specific examples of the substituted amino group include dicyanoethylamino, dimethoxyethylamino, dialkylamino, diphenylamino, dioctylamino, and dicyclohexylamino.

The aryl group represented by X is preferably an aryl group having 6 to 36 carbon atoms, and more preferably a phenyl group or a naphthyl group. Specific examples of the aryl group include phenyl, 4-t-butylphenyl, 2-methylphenyl, 2,4,6-trimethylphenyl, 2-methoxyphenyl, 4-methoxyphenyl, 2,6-dichlorophenyl, 2-chlorophenyl, 2,4-dichlorophenyl, and naphthyl.

Hereinbelow, specific examples of the compounds represented by formula (I), (II), or (III) are shown, but the present invention is not limited to them.

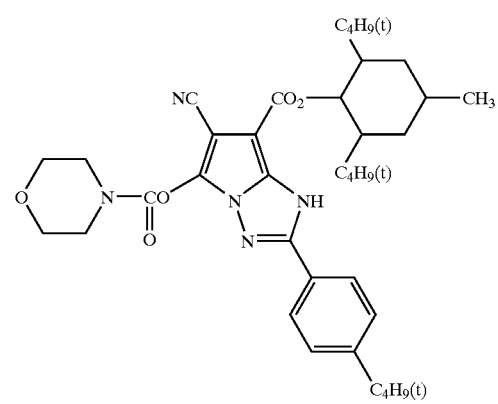
(I)-(1)
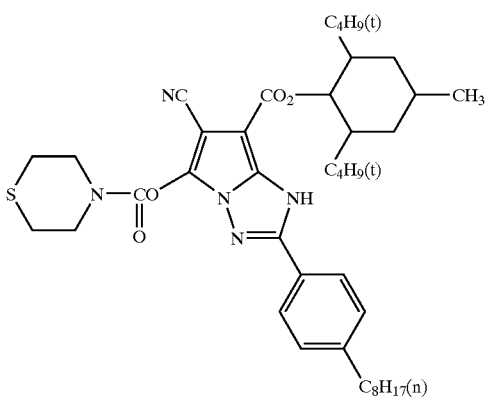
(I)-(5)
(I)-(2)
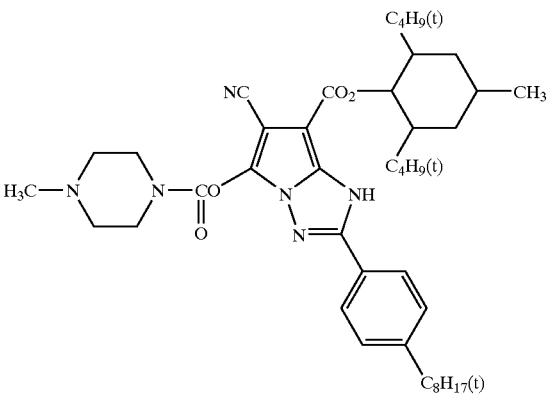
(I)-(6)
(I)-(3)
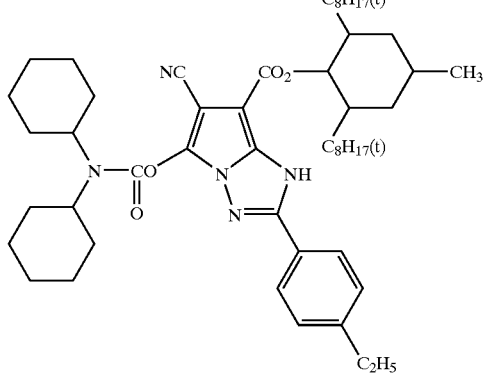
(I)-(7)
(I)-(4)
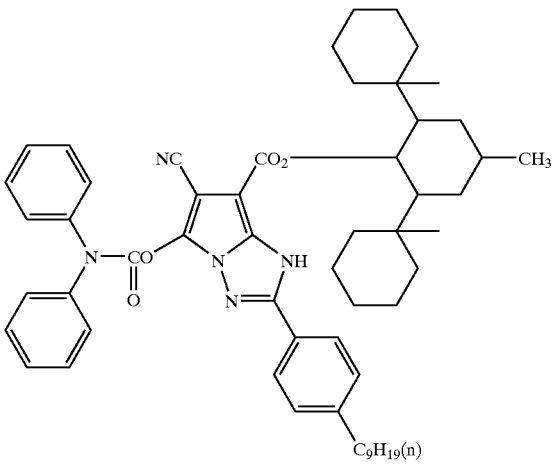
(I)-(8)

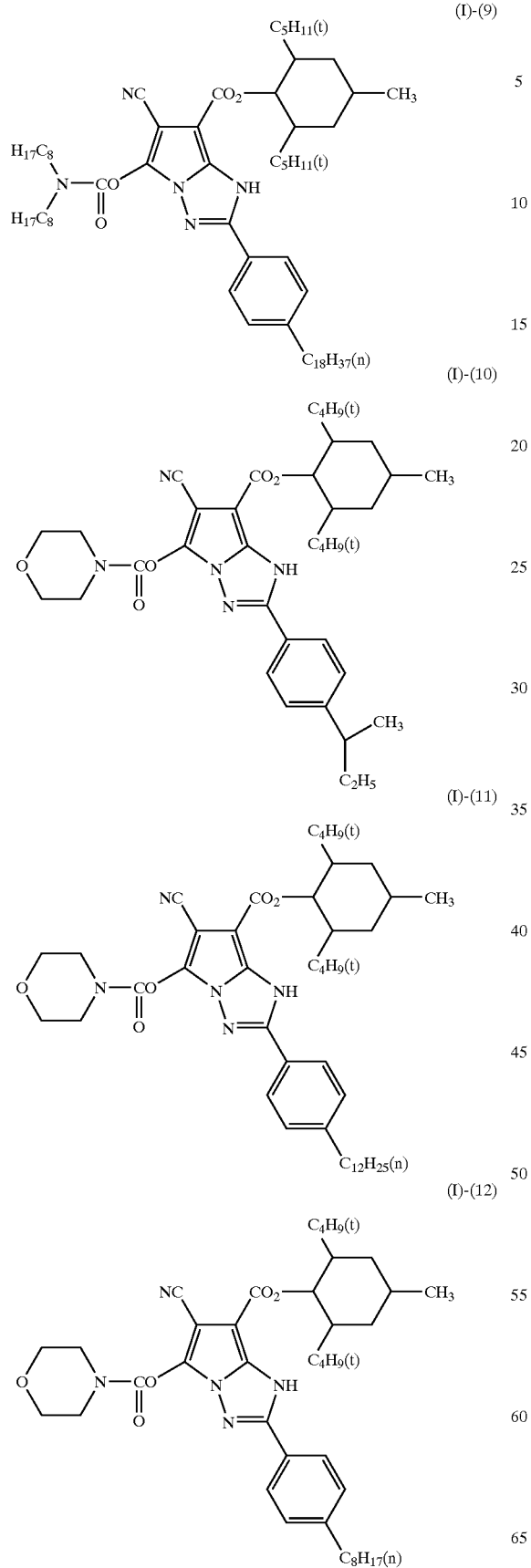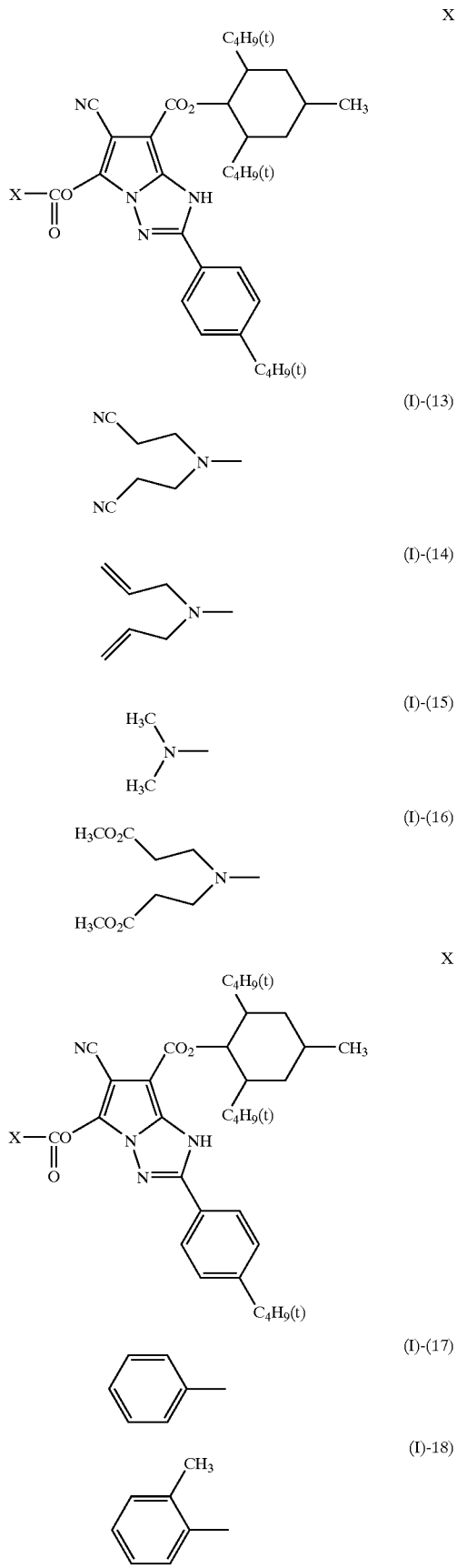

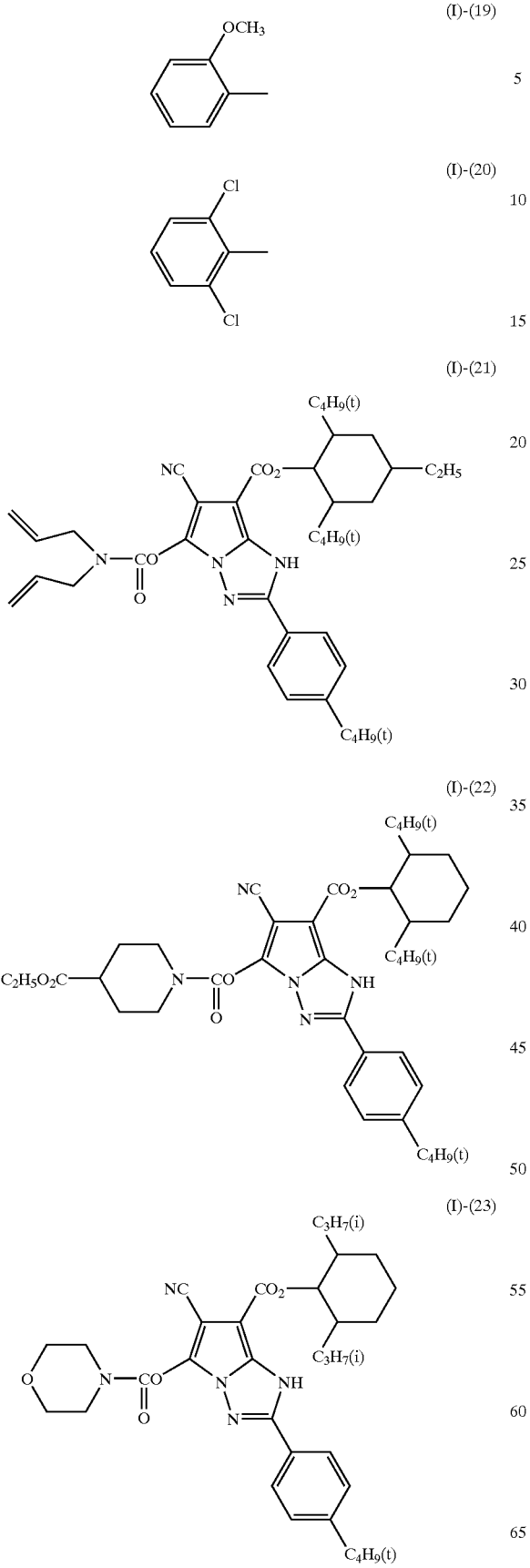
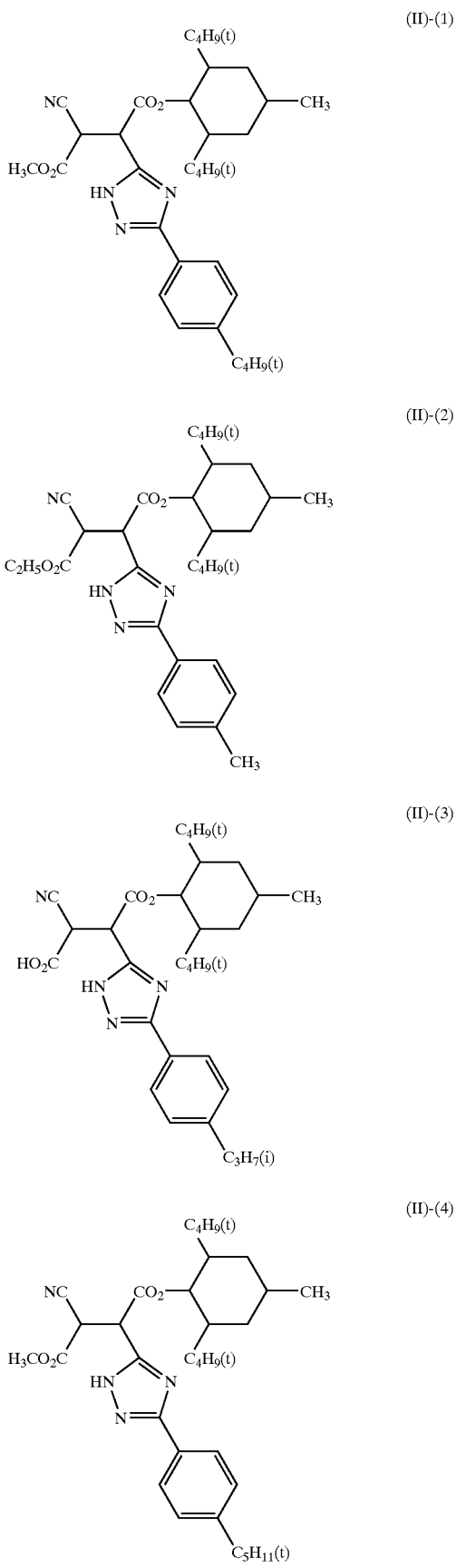

(II)-(5)
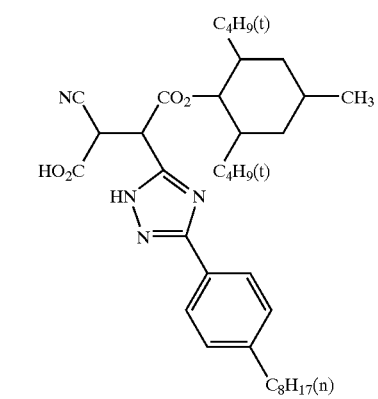
(II)-(6)
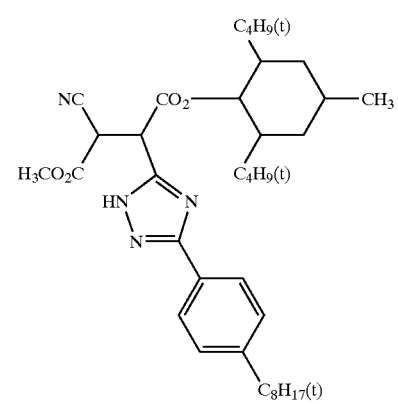
(II)-(7)
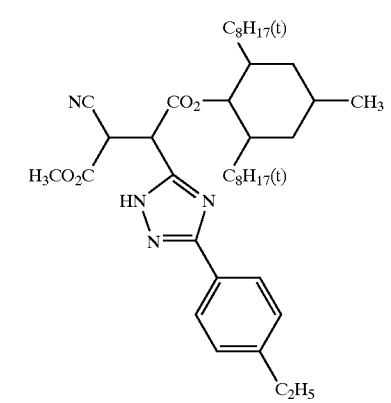
(II)-(8)
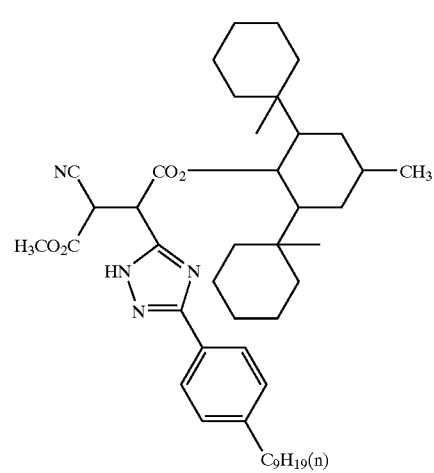
(II)-(9)
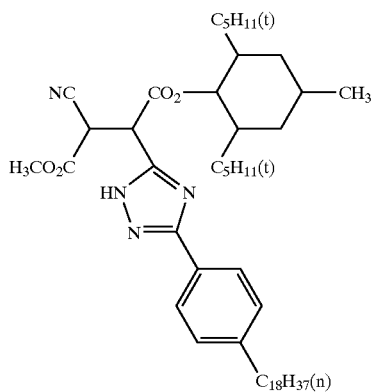
(II)-(10)
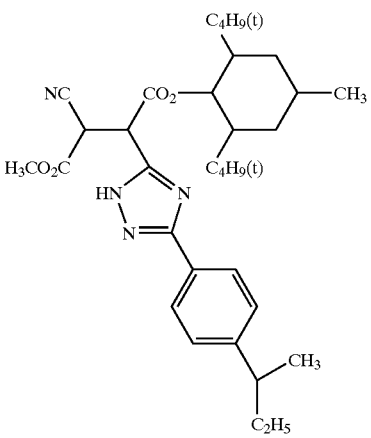
(II)-(11)
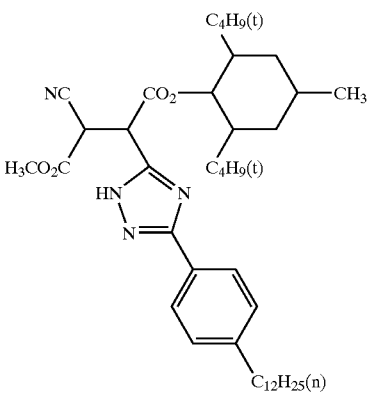
(II)-(12)
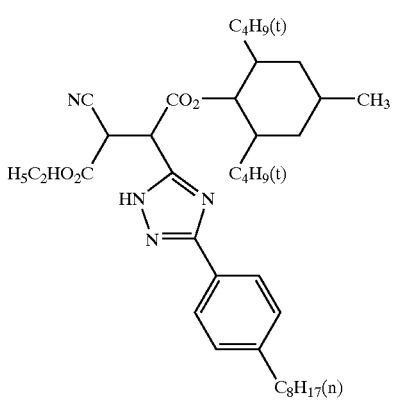

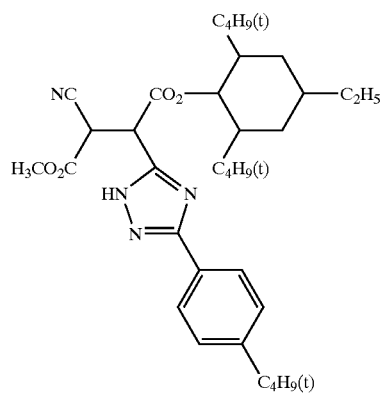 (II)-(21)
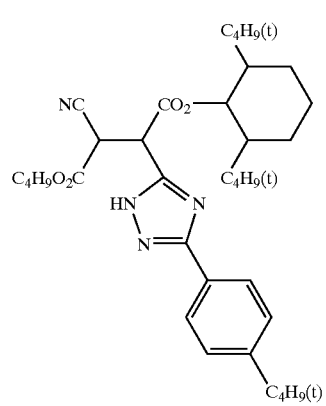 (II)-(22)
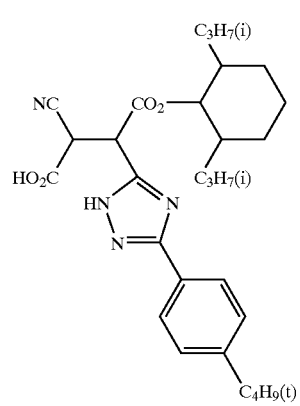 (II)-(23)
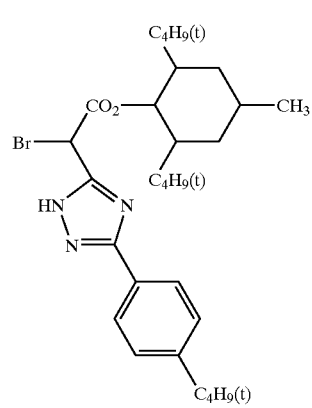 (III)-(1)
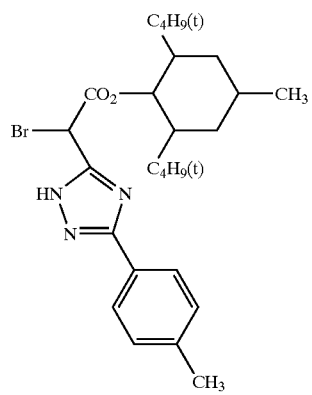 (III)-(2)
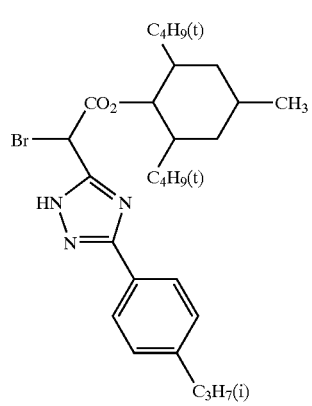 (III)-(3)
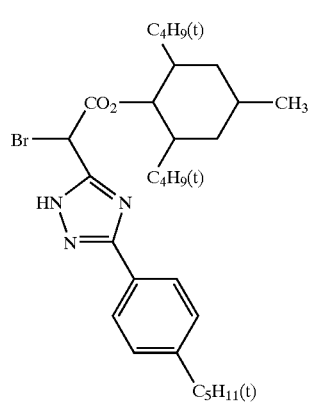 (III)-(4)
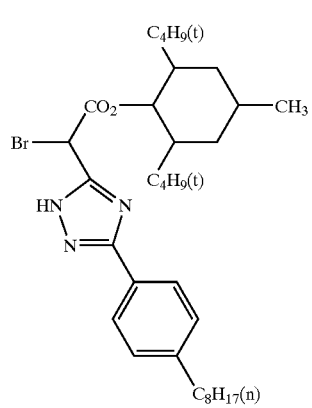 (III)-(5)

-continued (III)-(6)

(III)-(7)

(III)-(8)

(III)-(9)

(III)-(10)

(III)-(11)

(III)-(12)

(III)-(21)

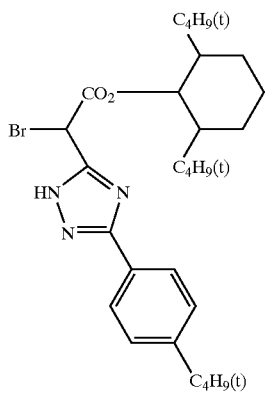

(III)-(22)

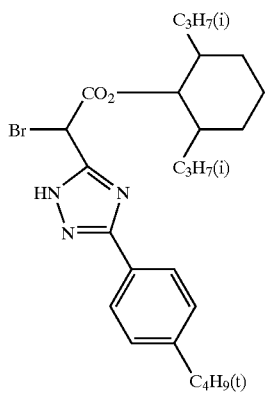

(III)-(23)

Now, general methods for synthesizing the compounds represented by one of formulae (I), (II), and (III) are described by reference to the below-shown scheme. The below-described Scheme 1 is a scheme in which Compound e, as the compound represented by formula (IV), Compound (III)-(1), as the compound represented by formula (III), methyl cyanoacetate, as cyanoacetates, Compound (II)-(1), as the compound represented by formula (II), and Compound (I)-(1), as the compound represented by formula (I), are used. As is shown in this Scheme 1, the compound represented by formula (III) can be obtained by halogenating the compound represented by the below-shown formula (IV). (Hereinafter, this step is referred to as Step 1.)

Further, the compound represented by formula (II) can be obtained by reacting the compound represented by formula (III) and cyanoacetates, by using a suitable organic base. (Step 2)

One compound represented by formula (II) in which $R_5$ is a hydrogen atom, can be easily obtained by hydrolyzing the ester product obtained in the above manner. (Step 3)

By allowing the thus-obtained compound represented by formula (II) ($R_5$ is hydrogen) to be subjected to the action of an acid halide (having the below-shown formula (V)) in the presence of a base, a 1H-pyrrole-[1,2,b][1,2,4] triazole derivative represented by formula (I) can be obtained. (Step 4)

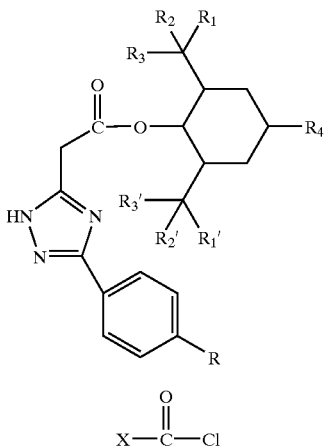

formula (IV)

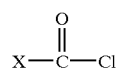

formula (V)

wherein $R_1$, $R_2$, $R_3$, $R_4$, $R_1'$, $R_2'$, $R_3'$, R, and X have the same meanings as those of formula (I).

Now, each of the steps is described in detail.

First, Step 1 is described in detail. In Step 1, the triazole derivative represented by formula (IV) can be synthesized by known methods; for example, methods described in J.C.S., 1961, page 518; J.C.S., 1962, page 5149; Angew, Chem, Vol. 72, page 956 (1960); Berichte., Vol. 97, page 3436 (1964), etc., methods described in documents cited in those documents, or similar methods. Preferably, the triazole derivative represented by formula (IV) can be synthesized by the method of the present invention described herein.

Examples of the halogenating agent in the halogenation of Step 1 include sulfuryl chloride, copper(II) chloride, N-chlorosuccinimide, N-bromosuccinimide, 1,3-dibromo-5,5-dimethylhidantoin, bromide, and pyridinium bromide perbromide, with preference given to sulfuryl chloride, bromine, 1,3-dibromo-5,5-dimethylhidantoin, and pyridinium bromide perbromide, and more preference given to bromine and 1,3-dibromo-5,5-dimethylhidantoin.

The molar ratio of the halogenating agent to formula (IV) in Step 1 is generally from 0.5 to 5, and preferably 0.5 to 2.0.

As the solvent used in Step 1, methylene chloride, chloroform, 1,2-dichloroethane, carbon tetrachloride, tetrahydrofuran, dioxane, benzene, toluene, ethyl acetate, N,N-dimethylformamide, N,N-dimethylacetamide, N-methylpyrrolidone, acetonitrile, and dimethyl sulfoxide can be mentioned. Preferable solvents are toluene, ethyl acetate, and acetonitrile.

In Step 1, if the reaction is carried out using a suitable base, the yield can be increased. As the base, triethylamine, diisopropylethylamine, pyridine, 2,6-lutidine, 2,4-lutidine, 2,3-lutidine, 2,5-lutidine, 2,4,6-collidine, 2-picoline, 3-picoline, 4-picoline, imidazole, dimethylaniline, piperidine, morpholine, N-methylmorpholine, tetramethylguanidine, and tetraphenylguanidine can be mentioned, with preference given to pyridine, 2,6-lutidine, 2,4,6-collidine, and 2-picoline.

The amount of the base is such that the molar ratio thereof to the compound represented by formula (IV) is generally from 0.5 to 5.0, and preferably from 0.5 to 2.0.

In Step 1, the reaction temperature is generally −10 to 80° C., and preferably 0 to 30° C. The reaction time is generally 1 min to 24 hours, preferably 10 min to 10 hours, and more preferably 30 min to 6 hours.

Now, Step 2 is described in detail.

As the base used in the nucleophilic substitution reaction of the compound represented by formula (III) and the cyanoacetates, n-butyllithium, t-butyllithium, lithium diisopropylamide, sodium hydride, potassium hydride, lithium hydride, t-butoxypotassium, sodium methoxide, sodium ethoxide, potassium methoxide, lithium methoxide, tetramethylguanidine, tetraphenylguanidine, 1,8-diazabicyclo[5.4.0]undec-7-ene (DBU), 1,5-diazabicyclo[4.3.0]non-5-ene (DBN), sodium hydroxide, and potassium hydroxide can be mentioned, with preference given to sodium hydride, sodium methoxide, sodium ethoxide, and t-butoxypotassium.

The molar ratio of the base used in Step 2 to the cyanoacetates is generally from 1.0 to 10, preferably 1.0 to 5.0, and more preferably 1.5 to 3.0.

The molar ratio of the cyanoacetates used in Step 2 to the compound represented by formula (III) is generally from 1.0 to 10, preferably from 1.0 to 5.0, and more preferably from 1.5 to 3.0.

As the solvent used in Step 2, hexane, methanol, methylene chloride, chloroform, 1,2-dichloroethane, carbon tetrachloride, tetrahydrofuran, dioxane, benzene, toluene, ethyl acetate, N,N-dimethylformamide, N,N-dimethylacetamide, N-methylpyrrolidone, acetonitrile, and dimethyl sulfoxide can be mentioned, with preference given to acetonitrile, N,N-dimethylformamide, N,N-dimethylacetamide, ethyl acetate, hexane, and methanol.

In Step 2, the reaction temperature is generally −78 to 150° C., preferably −40 to 60° C., and more preferably 20 to 30° C.

The reaction time is generally 1 min to 24 hours, preferably 10 min to 10 hours, and more preferably 30 min to 6 hours.

In the reaction in Step 2, the order of the addition is preferably carried out as follows: the compound of formula (III) previously dissolved in a solvent is added, dropwise, into the solvent containing the cyanoacetates and the base.

Step 3 is now described in detail.

The hydrolysis of the ester moiety of the compound represented by formula (II) can be carried out easily in a usual manner. As a general method, a method wherein a base is used can be employed. In that case, as the base, for example, sodium hydroxide, potassium hydroxide, lithium hydroxide, sodium carbonate, potassium carbonate, barium hydroxide, or ammonium carbonate is used, with preference given to sodium hydroxide and potassium hydroxide.

As the reaction medium, those solvents mentioned above are preferable, and more preferably a water/methanol mixed solvent is used.

The reaction temperature is generally 0 to 100° C., preferably 15 to 80° C., more preferably 30 to 80° C., and further preferably 40 to 80° C.

The reaction time is generally 1 min to 24 hours, preferably 10 min to 10 hours, and more preferably 30 min to 3 hours.

Now, Step 4 is described in detail.

As the base used in Step 4, can be mentioned, for example, triethylamine, diisopropylethylamine, pyridine, 2,6-lutidine, 2,4-lutidine, 2,3-lutidine, 2,5-lutidine, 2,4,6-collidine, 2-picoline, 3-picoline, 4-picoline, imidazole, dimethylaniline, piperidine, morpholine, N-methylmorpholine, tetramethylguanidine, tetraphenylguanidine, DBU, DBN, sodium hydroxide, potassium hydroxide, sodium carbonate, and potassium carbonate, with preference given to pyridine, triethylamine, lutidines, collidine, and picolines.

The molar ratio of the base used in Step 4 to the compound represented by formula (II) ($R_5$=H) is generally from 0.1 to 10, preferably 1.0 to 8.0, and more preferably 2.0 to 6.0.

Specific examples of the acid halides represented by formula (V) used in Step 4 include benzoyl chloride, 2-methylbenzoyl chloride, 2-methoxybenzoyl chloride, 2,6-dichlorobenzoyl chloride, dimethylcarbonic acid chloride, diethylcarbonic acid chloride, diphenyl carbonic acid chloride, dicyclohexylcarbonic acid chloride, dicyanoethylcarbonic acid chloride, dimethoxyethylcarbonic acid chloride, diallylcarbonic acid chloride, morpholinocarbonyl chloride, and 4-methoxycarbonylisonicotincarbonyl chloride.

The molar ratio of the acid halide represented by formula (V) used in Step 4 to the compound represented by formula (II) is generally from 1.0 to 10, preferably from 1 to 5, and more preferably from 2 to 4.

As the solvent used in Step 4, methylene chloride, chloroform, 1,2-dichloroethane, carbon tetrachloride, tetrahydrofuran, dioxane, benzene, toluene, ethyl acetate, N,N-dimethylformamide, N,N-dimethylacetamide, N-methylpyrrolidone, acetonitrile, and dimethyl sulfoxide can be mentioned, with preference given to acetonitrile, N,N-dimethylformamide, N,N-dimethylacetamide, ethyl acetate, and toluene.

In Step 4, the reaction temperature is generally −78 to 100° C., preferably −20 to 80° C., and more preferably 0 to 50° C.

The reaction time is generally 1 min to 24 hours, preferably 15 min to 10 hours, and more preferably 30 min to 6 hours.

Now, the production method of the intermediate of the present invention is described in detail.

In formula (VI), $R_{11}$ represents a hydrogen atom, or a straight-chain, branched-chain or cyclic alkyl group having 1 to 36 carbon atoms, such as methyl, ethyl, propyl, isopropyl, isobutyl, t-butyl, octyl, octadecyl, or cyclohexyl.

$R_{11}$ preferably represents a straight-chain or branched-chain alkyl group having preferably 1 to 24 carbon atoms and more preferably 1 to 12 carbon atoms, or a cyclic alkyl group (preferably having 3 to 8 carbon atoms), which may be substituted. Preferable substituents are a halogen atom, a hydroxyl group, a cyano group, a nitro group, a carboxyl group, an amino group, an alkoxy group, an aryloxy group, a heterocyclic oxy group, an acylamino group, an alkylamino group, an anilino group, a ureido group, a sulfamoylamino group, an alkylthio group, an arylthio group, a heterocyclic thio group, an alkoxycarbonylamino group, an aryloxycarbonylamino group, a sulfonamido group, a carbamoyl group, a sulfamoyl group, a sulfonyl group, an alkoxycarbonyl group, an aryloxycarbonyl group, an acyloxy group, a carbamoyloxy group, a silyloxy group, an imino group, a sulfinyl group, and a phosphonyl group. Particularly preferably, $R_{11}$ represents a methyl group.

$R_{12}$, $R_{13}$, $R_{14}$, $R_{12}'$, $R_{13}'$, and $R_{14}'$, each represent a hydrogen atom, a straight-chain or branched-chain alkyl group having 1 to 24 carbon atoms, or a cyclic alkyl group (preferably having 3 to 8 carbon atoms).

$R_{12}$, $R_{13}$, $R_{14}$, $R_{12}'$, $R_{13}'$, and $R_{14}'$, which are the same or different, each represent a straight-chain or branched-chain alkyl group preferably having 1 to 12 carbon atoms, and more preferably 1 to 6 carbon atoms, or a cyclic alkyl group (preferably having 3 to 8 carbon atoms), such as methyl, ethyl, propyl, and cyclohexyl. $R_{12}$ and $R_{13}$, and $R_{12}'$ and $R_{13}'$ may bond together to form a ring (for example a 3- to 6-membered ring, preferably a 6-membered ring, such as cyclohexyl), respectively. Particularly preferably, $R_{12}$, $R_{13}$, $R_{14}$, $R_{12}'$, $R_{13}'$, and $R_{14}'$ each represent a methyl group.

In some cases, the compounds used in the present invention have sterochemical isomers, and in the present invention, use can be made of each of the compounds in the form of mixtures of stereoisomers or in the form of a single stereoisomer.

Specific examples of the compound (VI) are shown below, but the present invention is not restricted to them.

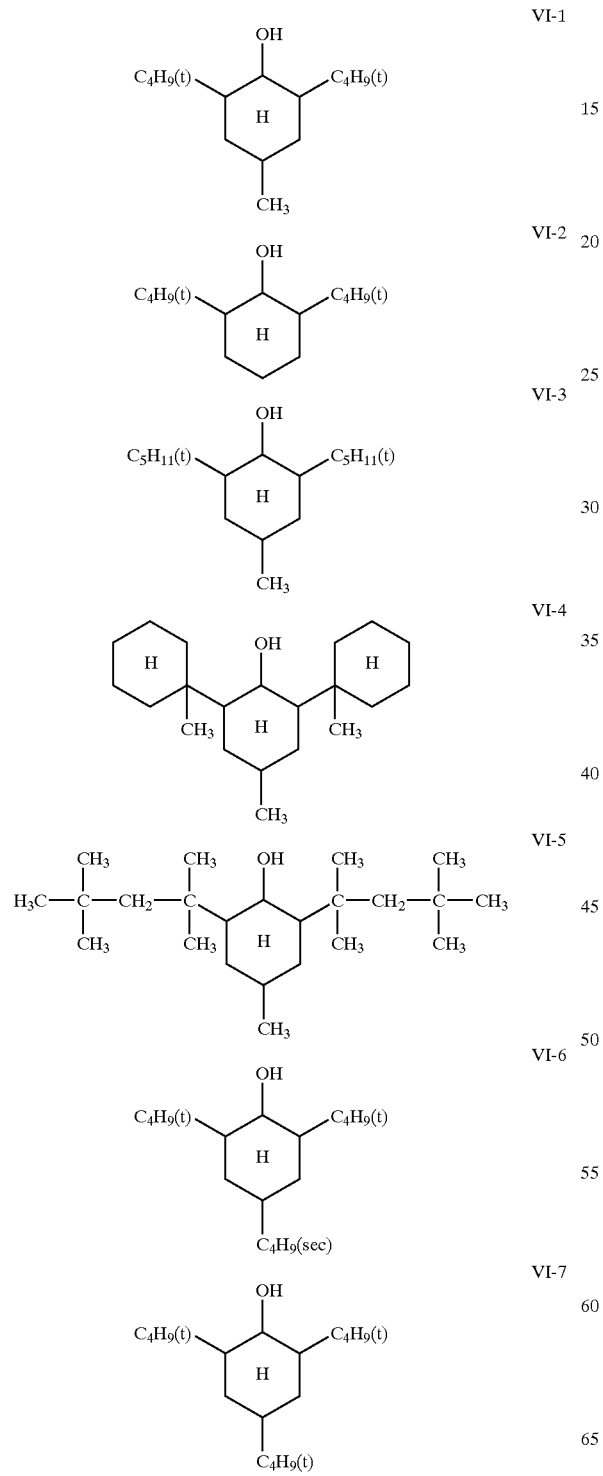

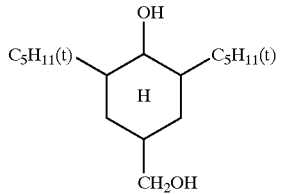

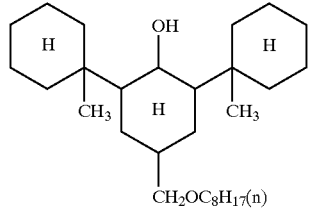

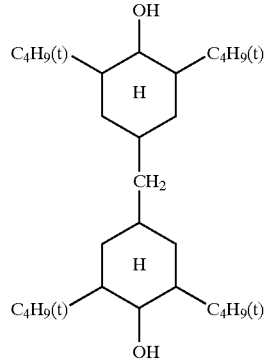

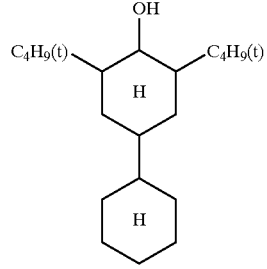

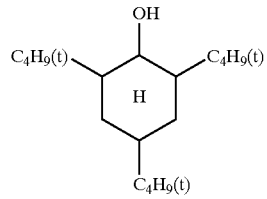

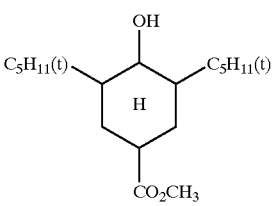

VI-14
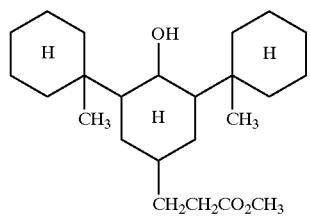
VI-15
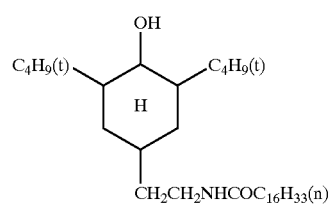
VI-16
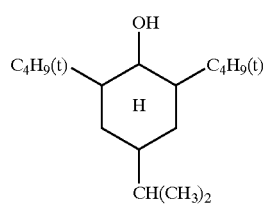
VI-17
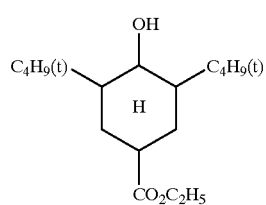
VI-18
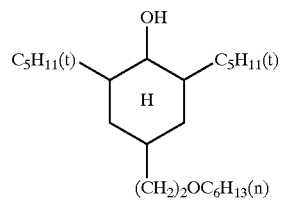
VI-19
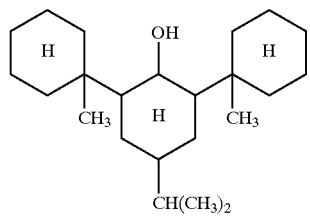
VI-20
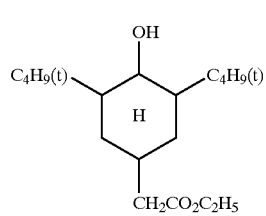
VI-21
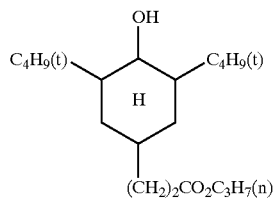
VI-22
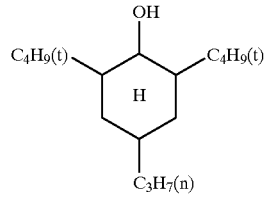
VI-23
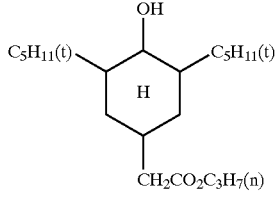
VI-24
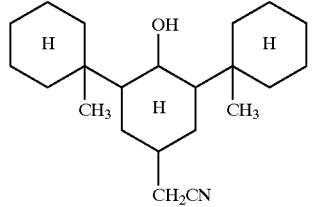
VI-25
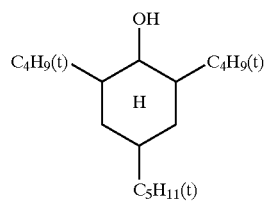
VI-26
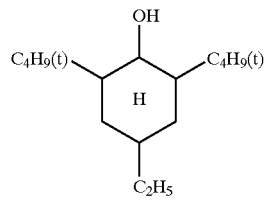
VI-27
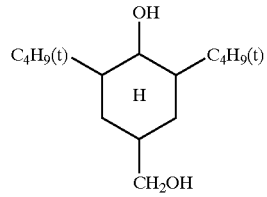

VI-28 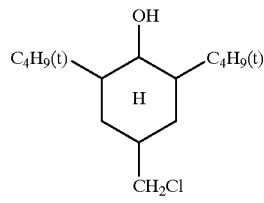
VI-29 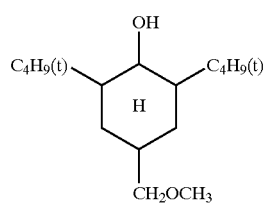
VI-30 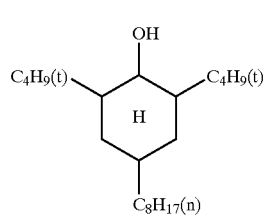
VI-31 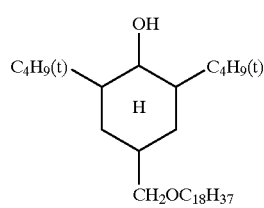
VI-32 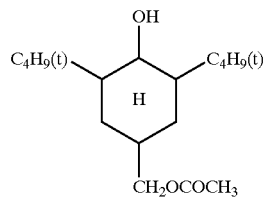
VI-33 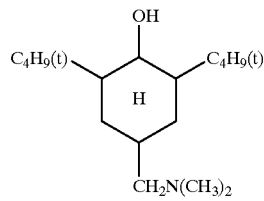
VI-34 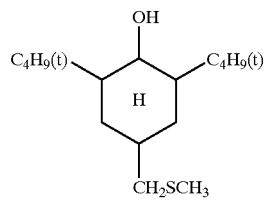
VI-35 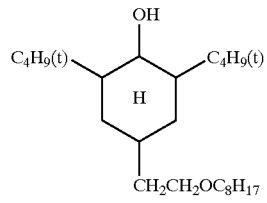
VI-36 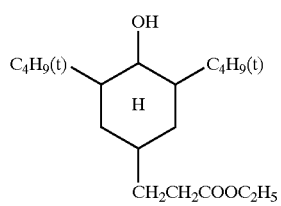
VI-37 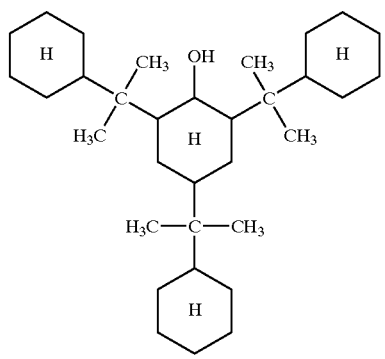
VI-38 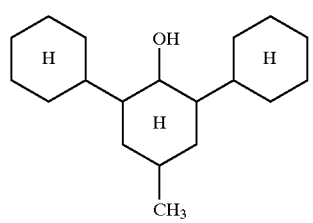
VI-39 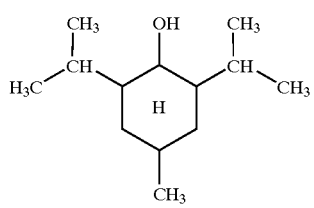
VI-40 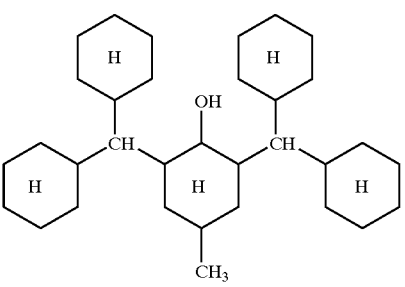

Now, formula (VII) is described.

$R_{15}$ and $R_{16}$, which are the same or different, each represent a hydrogen atom, a halogen atom (e.g., a chlorine atom, a bromine atom, and an iodine atom), an alkyl group [a straight-chain, branched-chain or cyclic alkyl group having 1 to 36 carbon atoms (preferably having 1 to 24 carbon atoms), which may be substituted by such a substituent as described for $R_{11}$, e.g., methyl, ethyl, propyl, butyl, isopropyl, octyl, hexadecyl, cyclohexyl, and 1-cyano-(methoxycarbonyl)methyl], or an aryl group [an aryl group having 6 to 36 carbon atoms (preferably having 6 to 24 carbon atoms), which aryl group may be substituted by such a substituent as described for $R_{11}$, e.g., a phenyl group].

Preferably at least one of $R_{15}$ and $R_{16}$ represents a hydrogen atom, and more preferably both of $R_{15}$ and $R_{16}$ each represent a hydrogen atom.

$R_{17}$ represents an aliphatic group or an aryl group. M represents a hydrogen atom (M=H and n=1), an alkali metal (M=Li, Na, K, Rb, or Cs, and n=1), or an alkali earth metal (M=Be, Mg, Ca, Sr, or Ba, and n=2).

The aliphatic group represented by $R_{17}$ is, for example, a straight-chain alkyl group, a branched-chain alkyl group, an aralkyl group, an alkenyl group, an alkynyl group, a cycloalkyl group, and a cycloalkenyl group, having 1 to 36 (preferably 1 to 24) carbon atoms, any of which groups may have such a substituent as described for $R_{11}$; more specifically, for example, methyl, ethyl, propyl, isopropyl, t-butyl, t-amyl, octyl, octadecyl, vinyl, cyclohexyl, 4-pentylcyclohexyl, cyclohexenyl, and propargyl.

The aryl group represented by $R_{17}$ is an aryl group having 6 to 36 carbon atoms (preferably 6 to 24 carbon atoms), with preference given to a phenyl group or a naphthyl group. The aryl group may have such a substituent as described for $R_{11}$, for example, phenyl, 3-nitrophenyl, 4-nitrophenyl, 4-chlorophenyl, 3,5-dichlorophenyl, 4-methoxyphenyl, 4-t-butylphenyl, 3-(2-octoxy-5-t-octylphenylsulfonamido)-4-methoxyphenyl, and 3-nitro-4-methylphenyl.

Preferably M represents a hydrogen atom (H), lithium (Li), sodium (Na), potassium (K), magnesium (Mg), or calcium (Ca), and more preferably a hydrogen atom (H), sodium (Na), or potassium (K).

Specific examples of the carbonic acids represented by formula (VII) are shown below, but the present invention is not restricted to them.

VII-1
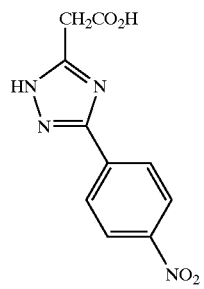

VII-2
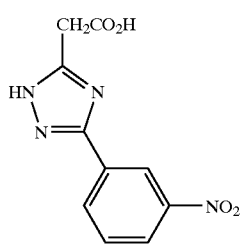

-continued

VII-3
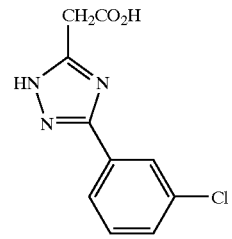

VII-4
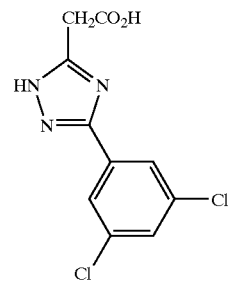

VII-5
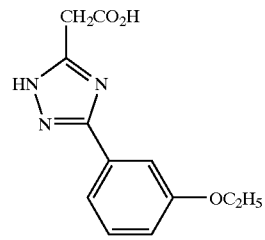

VII-6
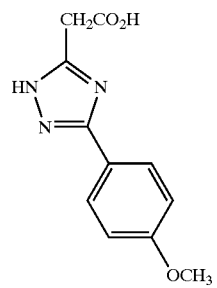

VII-7
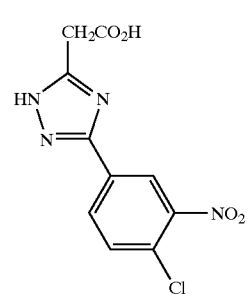

VII-8
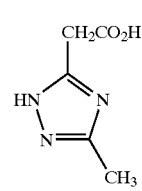

-continued

VII-9: 1H-1,2,4-triazole with CH₂CO₂H at 3-position and CH(CH₃)₂ at 5-position

VII-10: 1H-1,2,4-triazole with CH₂CO₂H and C₄H₉(t)

VII-11: 1H-1,2,4-triazole with CH₂CO₂H and CH(C₂H₅)C₄H₉(n)

VII-12: 1H-1,2,4-triazole with CH₂CO₂H and cyclohexyl

VII-13: 1H-1,2,4-triazole with CH₂CO₂H and CH₂CO₂C₂H₅

VII-14: 1H-1,2,4-triazole with CH₂CO₂H and CH(CH₃)CH₂–phthalimide

VII-15: 1H-1,2,4-triazole with CH₂CO₂H and C(CH₃)₂CO₂C₂H₅

-continued

VII-16: 1H-1,2,4-triazole with CH₂CO₂H and phenyl

VII-17: 1H-1,2,4-triazole with CH₂CO₂H and 3-nitro-4-methylphenyl

VII-18: 1H-1,2,4-triazole with CH₂CO₂H and 4-tert-butylphenyl

VII-19: 1H-1,2,4-triazole with CH₂CO₂H and substituted phenyl bearing NH–SO₂–(2-OC₈H₁₇(n), 5-C₈H₁₇(t))phenyl and OCH₃

VII-20: 1H-1,2,4-triazole with CH(CH₃)CO₂H and CH₂CO₂C₂H₅

VII-21: 1H-1,2,4-triazole with CH(C₂H₅)CO₂H and CH₂CO₂C₂H₅

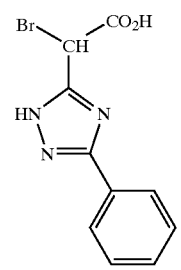 VII-22
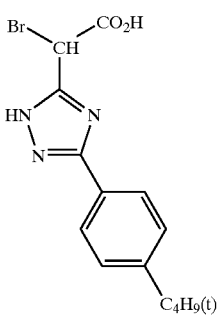 VII-23
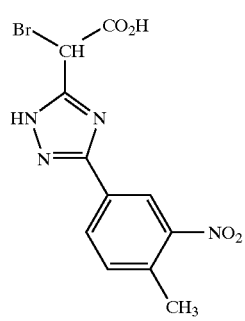 VII-24
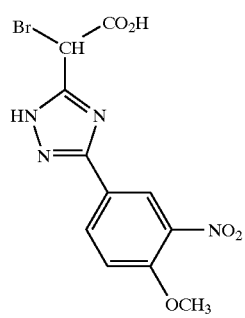 VII-25
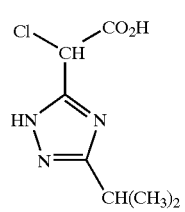 VII-26
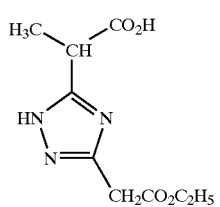 VII-27
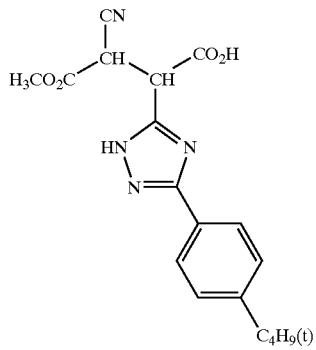 VII-28
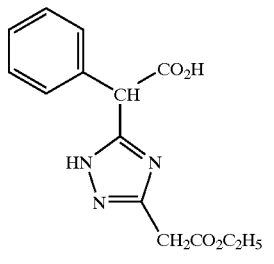 VII-29
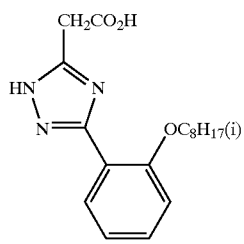 VII-30
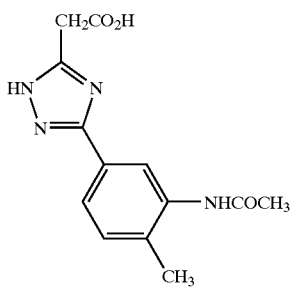 VII-31
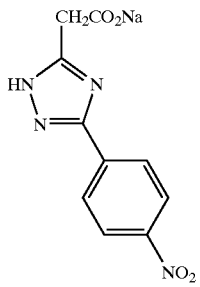 VII-32
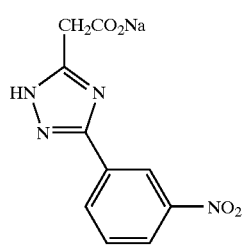 VII-33

VII-34
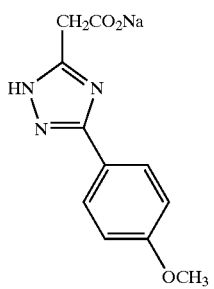
VII-35
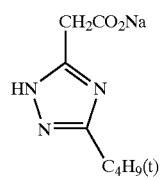
VII-36
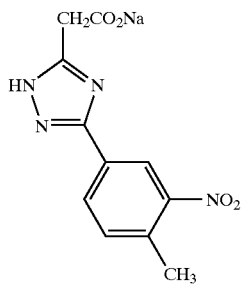
VII-37
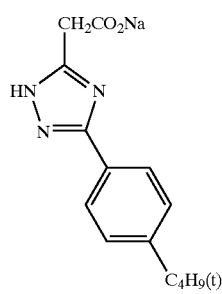
VII-38
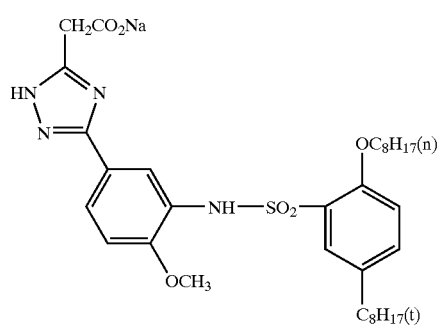
VII-39
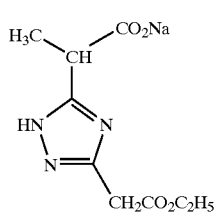
VII-40
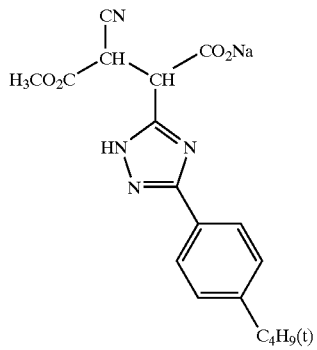
VII-41
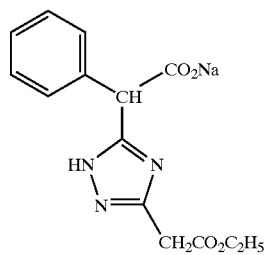
VII-42
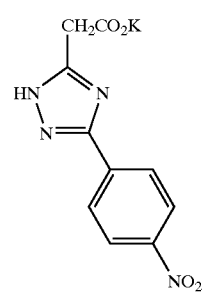
VII-43
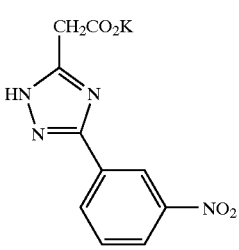
VII-44
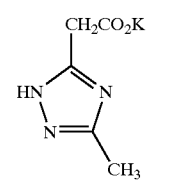
VII-45
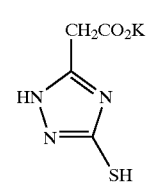

37

-continued

VII-46: 3-cyclohexyl-1H-1,2,4-triazol-5-yl acetic acid potassium salt (CH₂CO₂K on triazole, cyclohexyl substituent)

VII-47: 1H-1,2,4-triazole with CH₂CO₂K and CH₂CO₂C₂H₅ substituents

VII-48: 5-(4-methyl-3-nitrophenyl)-1H-1,2,4-triazol-3-yl acetic acid potassium salt VII-49: 5-(4-tert-butylphenyl)-1H-1,2,4-triazol-3-yl acetic acid potassium salt VII-50: triazole derivative with CH₂CO₂K, phenyl bearing NH–SO₂–(2-OC₈H₁₇, 5-C₈H₁₇(t))phenyl and OCH₃ substituents VII-51: H₃CO₂C–CH(CN)–CH(CO₂K)– attached to 5-(4-tert-butylphenyl)-1H-1,2,4-triazole

38

-continued

VII-52: 3-(n-octyl)-1H-1,2,4-triazol-5-yl acetic acid

VII-53: 3-(n-hexadecyl)-1H-1,2,4-triazol-5-yl acetic acid

VII-54: 3-(tert-butyl)-1H-1,2,4-triazol-5-yl acetate · 1/2 Mg²⁺

VII-55: 5-(2-methoxy-4-methylphenyl)-1H-1,2,4-triazol-3-yl acetic acid

VII-56: 5-(4-n-dodecyloxyphenyl)-1H-1,2,4-triazol-3-yl acetic acid

VII-57: 5-(4-n-decylphenyl)-1H-1,2,4-triazol-3-yl acetic acid

VII-58
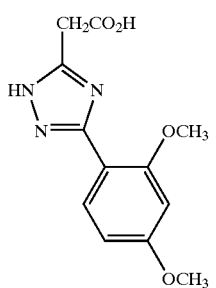
VII-59
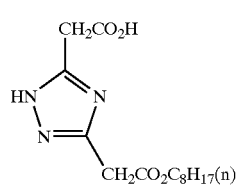
VII-60
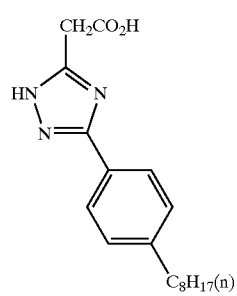
VII-61
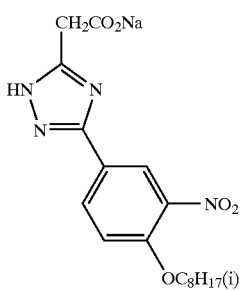
VII-62
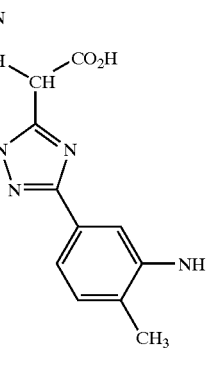
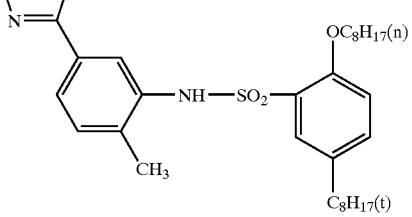
VII-63
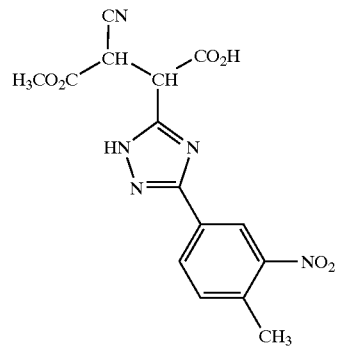
VII-64
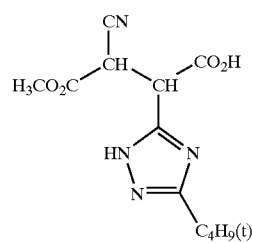
VII-65
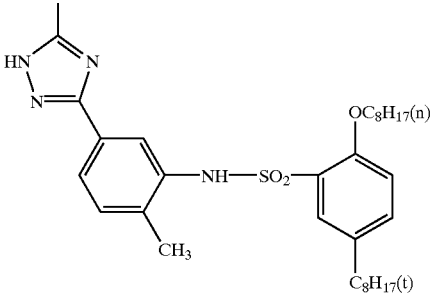
VII-66
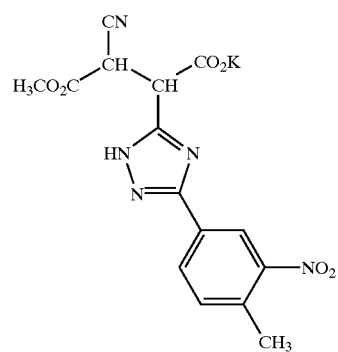
VII-67
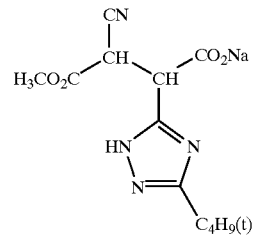

Now, formula (VIII) is described.

$R_{18}$ and $R_{19}$, which are the same or different, each represent a hydrogen atom, a halogen atom (preferably a chlorine atom, a bromine atom, and an iodine atom, and more preferably a chlorine atom), an alkyl group [a straight-chain or branched-chain alkyl group having 1 to 36 carbon atoms (preferably having 1 to 24 carbon atoms), or a cyclic alkyl group (preferably having 3 to 8 carbon atoms), each of which may be substituted by such a substituent as described for $R_{11}$, e.g., methyl, ethyl, propyl, butyl, t-butyl, isopropyl, hexyl, octyl, hexadecyl, cyclohexyl, and cyclopentyl], or an aryl group [an aryl group having 6 to 36 carbon atoms (preferably having 6 to 24 carbon atoms), which aryl group may be substituted by such a substituent as described for $R_{11}$, e.g., a phenyl group]. $R_{18}$ and $R_{19}$ may bond together to form a ring. Most preferably $R_{18}$ and $R_{19}$ each represent a hydrogen atom.

Specific examples of the carboxylic acid anhydrides represented by formula (VIII) that can be used in the present invention, are shown below, but the present invention is not restricted to them.

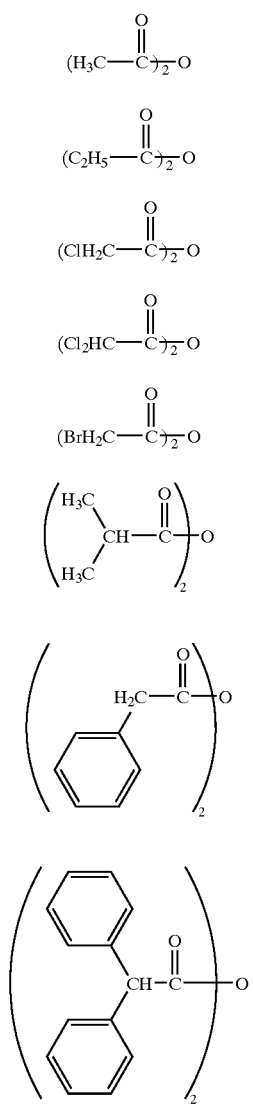

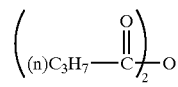

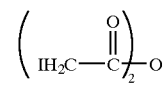

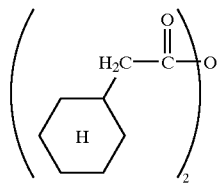

The production method of the present invention is shown by the following Scheme (i).

In the present invention, if the compound represented by formula (VIII) is acetic anhydride, a compound represented by the below-shown formula (X) is isolated. Therefore, the ester compound represented by formula (IX) is synthesized via the deacetylation reaction of the compound represented by formula (X). The compound (X) may be isolated, or the compound represented by formula (VI) and the compound represented by formula (VII) are condensed and the compound (IX) may be derived by the deacetylation reaction without treating the reaction system. The deacetylation reaction may be carried out under either acidic conditions or alkaline conditions.

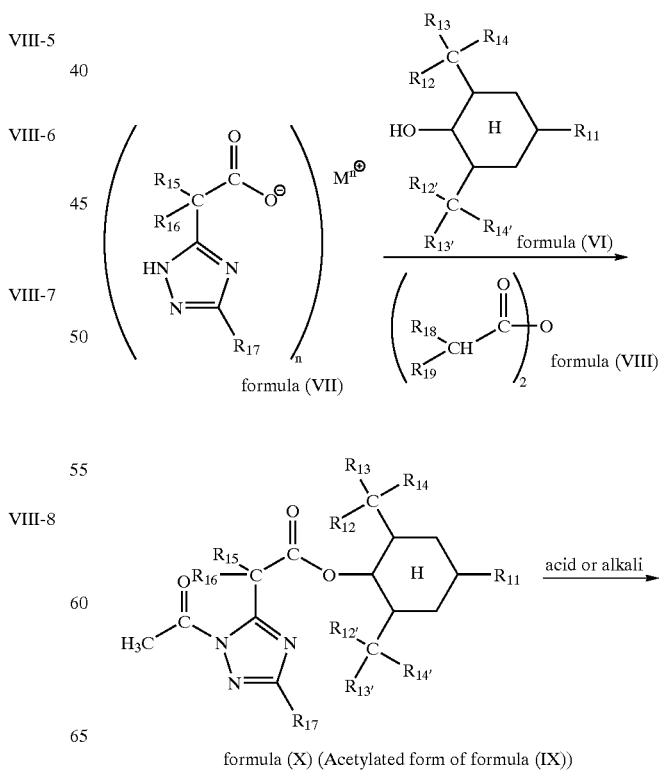

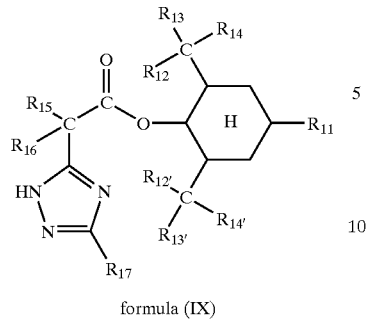

formula (IX)

To carry out the deacetylation under acidic conditions, for example, hydrochloric acid, sulfuric acid, trifluoroacetic acid, p-toluenesulfonic acid, or methanesulfonic acid can be used. To carry out the deacetylation under alkaline conditions, for example, aqueous ammonia, sodium hydroxide, potassium hydroxide, sodium methylate, sodium ethylate, potassium ethylate, or potassium t-butoxide can be used.

Specific examples of the ester compound represented by formula (IX) that can be synthesized by the method of the present invention are shown below, but the present invention is not restricted to them.

IX-1
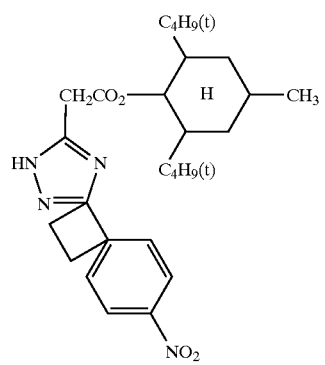

IX-2
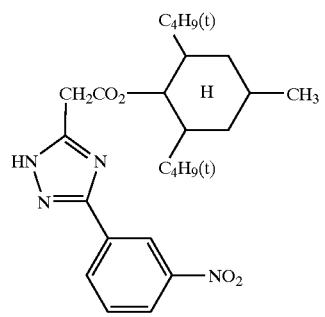

IX-3
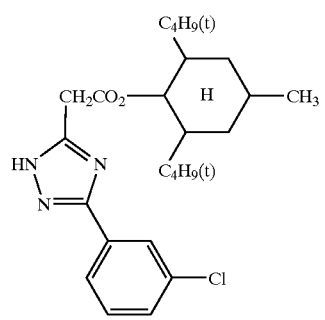

IX-4
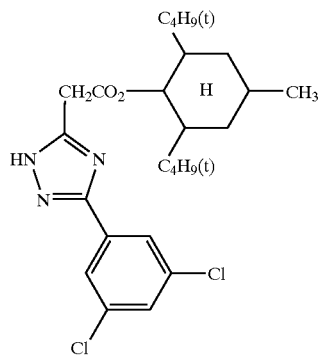

IX-5
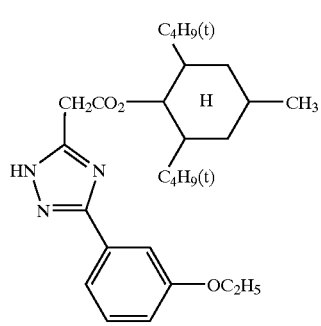

IX-6
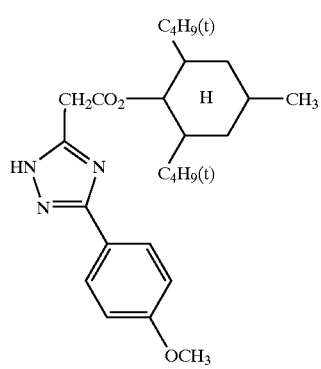

IX-7
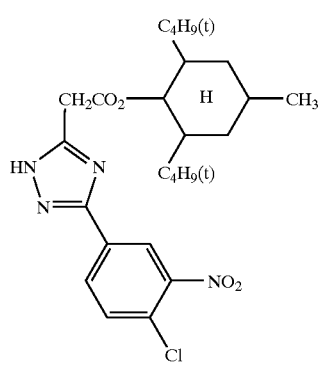

IX-8
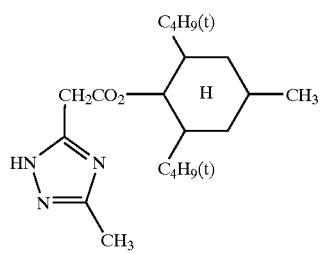

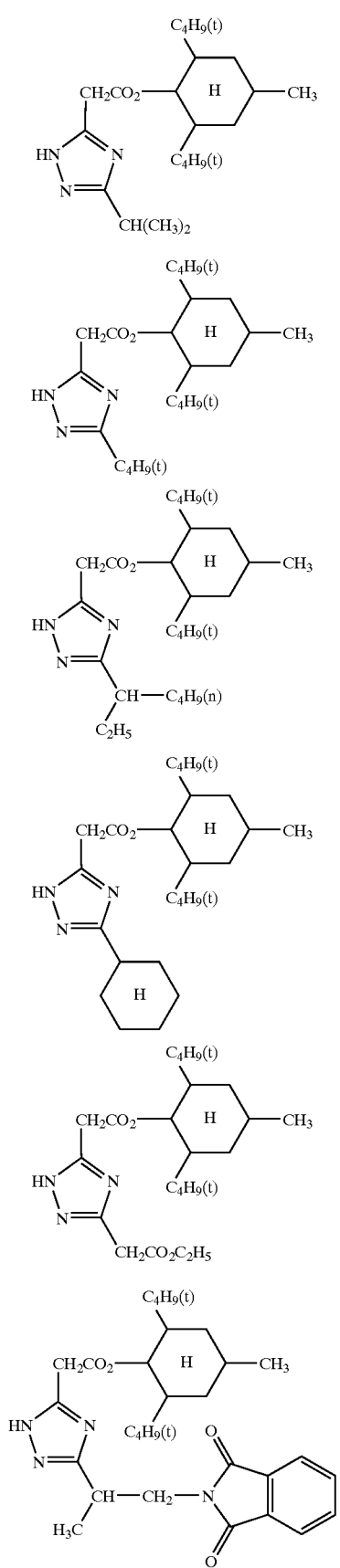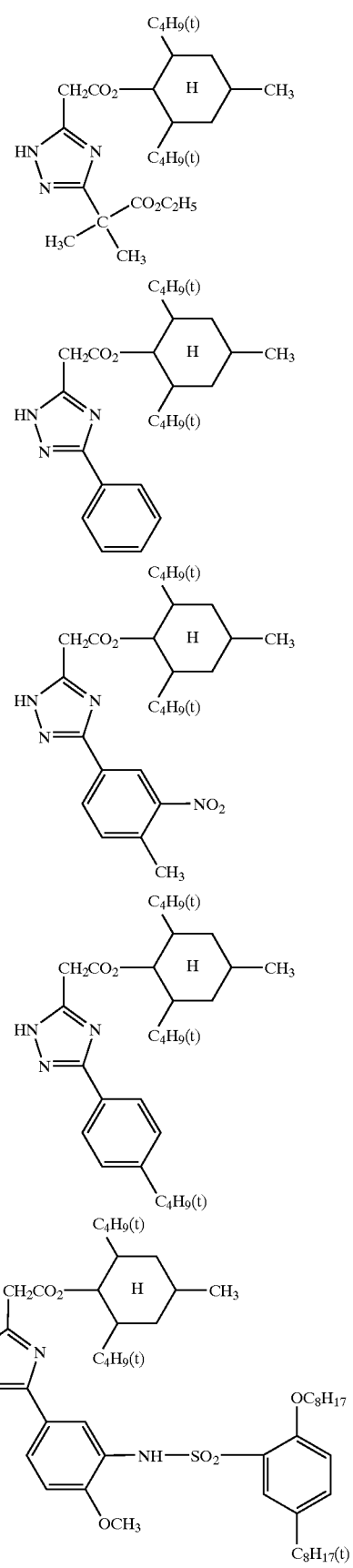

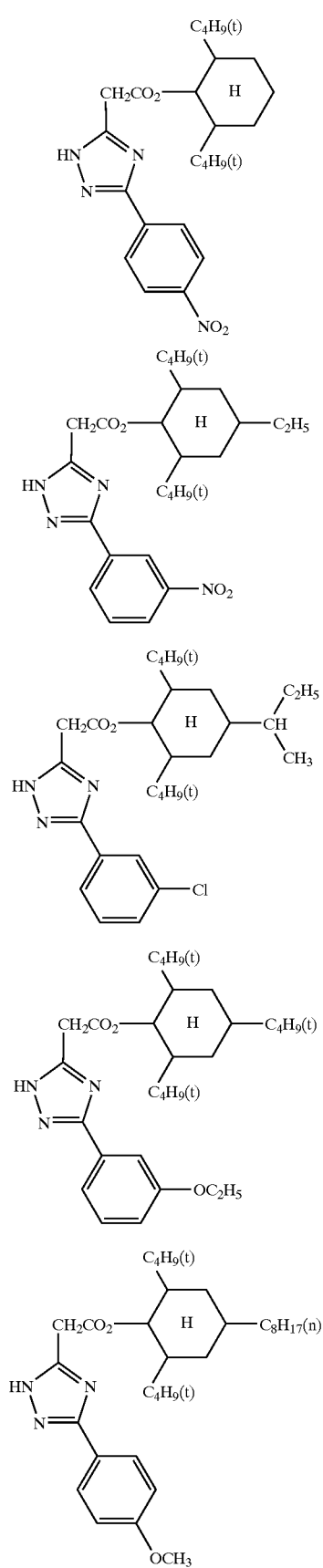
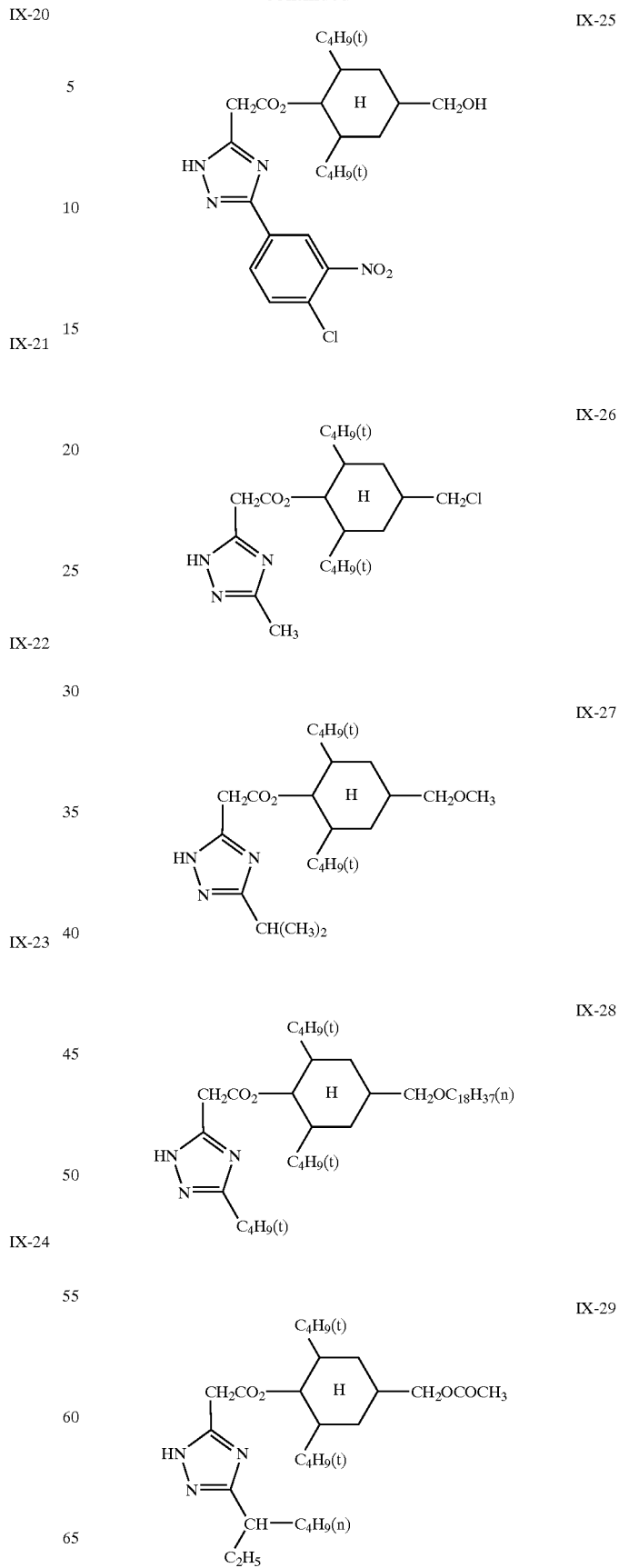

IX-30
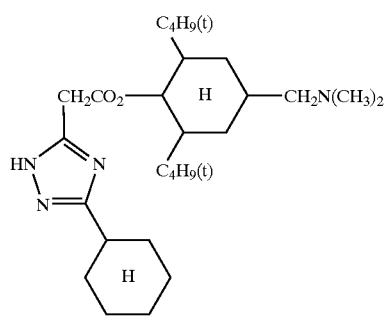
IX-31
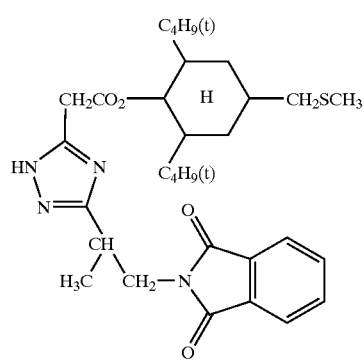
IX-32
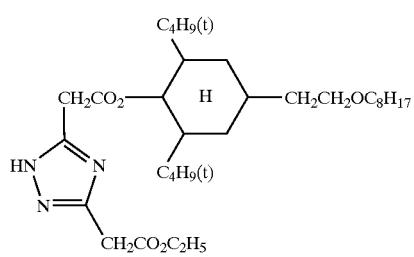
IX-33
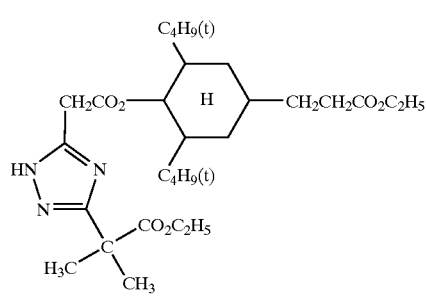
IX-34
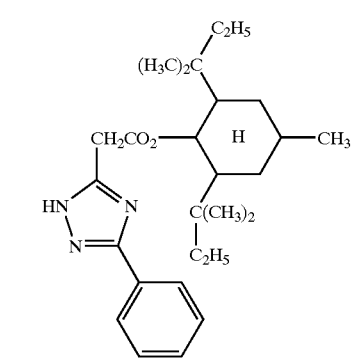
IX-35
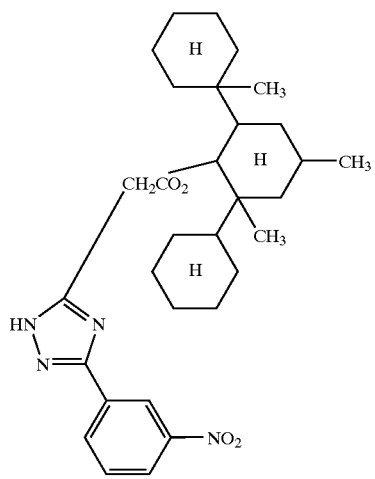
IX-36
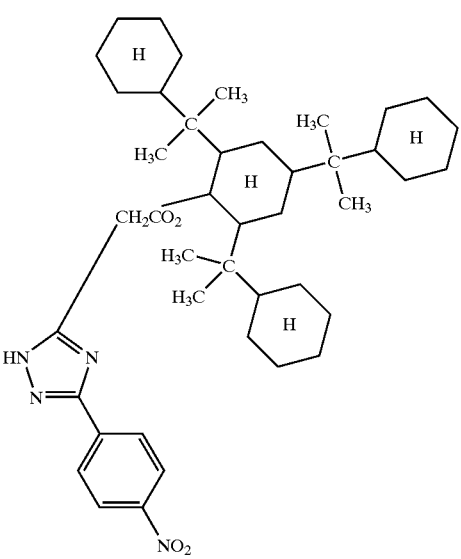
IX-37
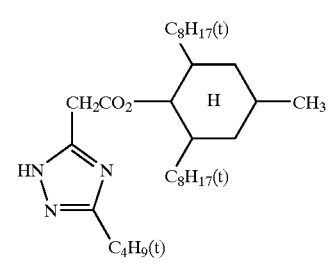
IX-38
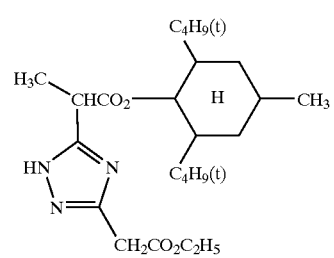

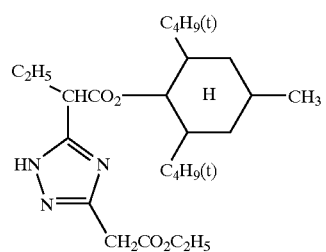
IX-39
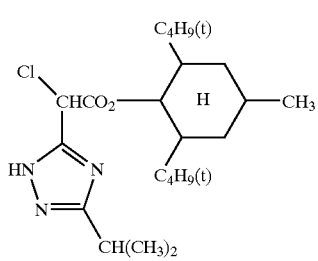
IX-44
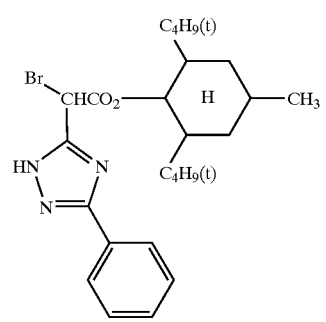
IX-40
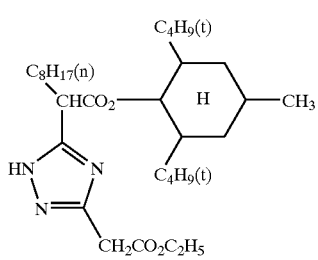
IX-45
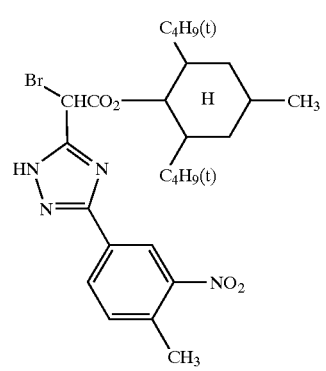
IX-41
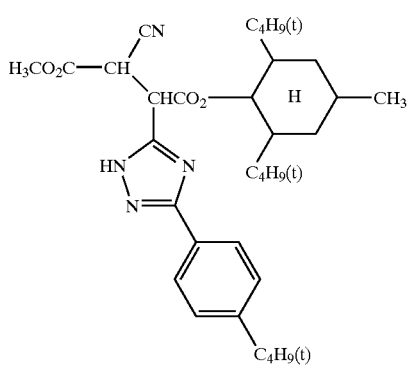
IX-46
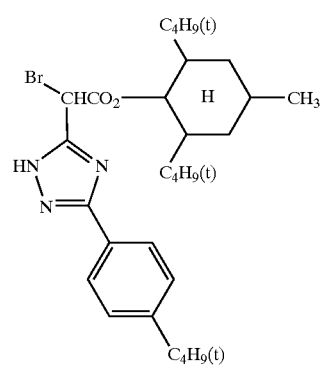
IX-42
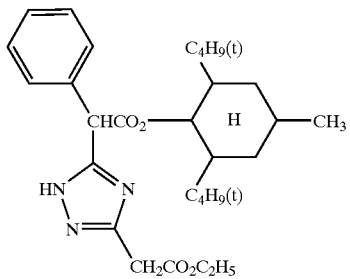
IX-47
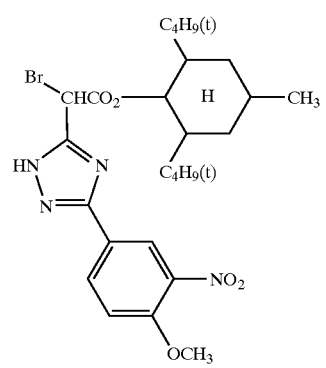
IX-43
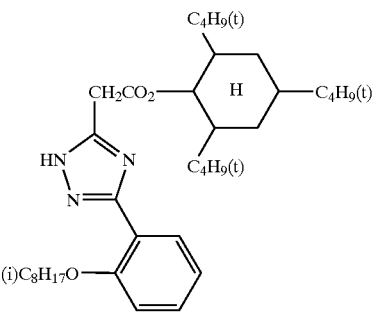
IX-48

IX-49
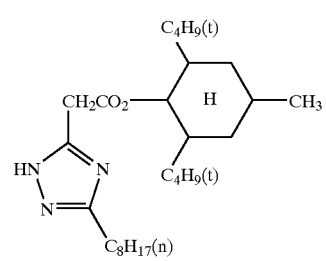
IX-50
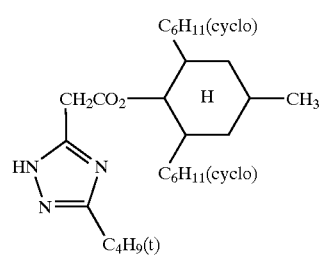
IX-51
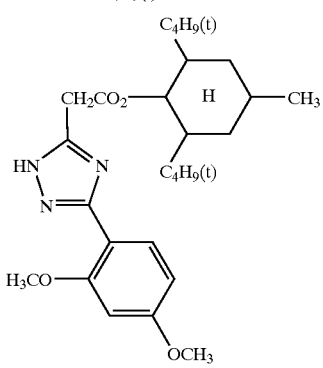
IX-52
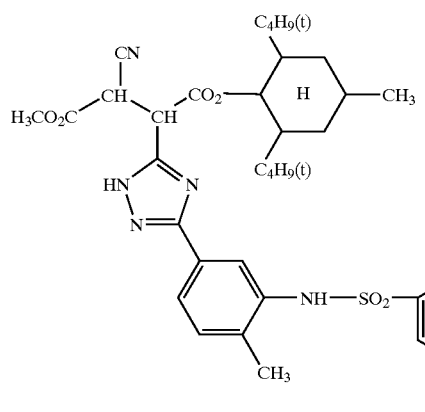
IX-53
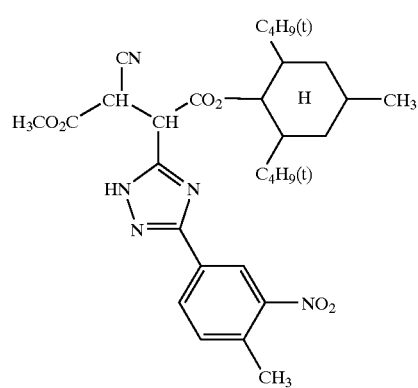
IX-54
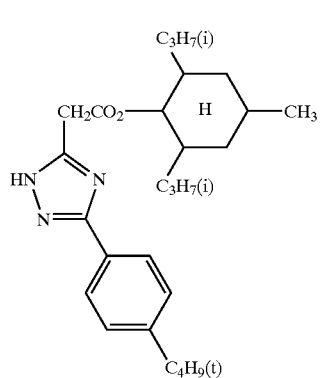
IX-55
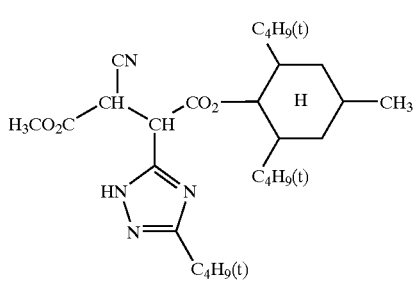
IX-56
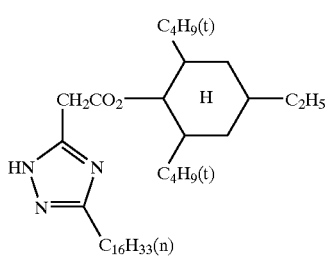
IX-57
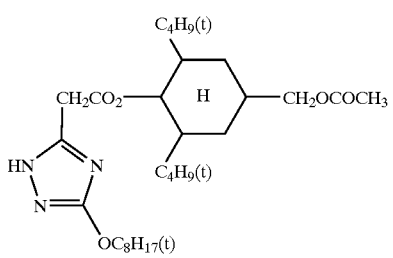
IX-58

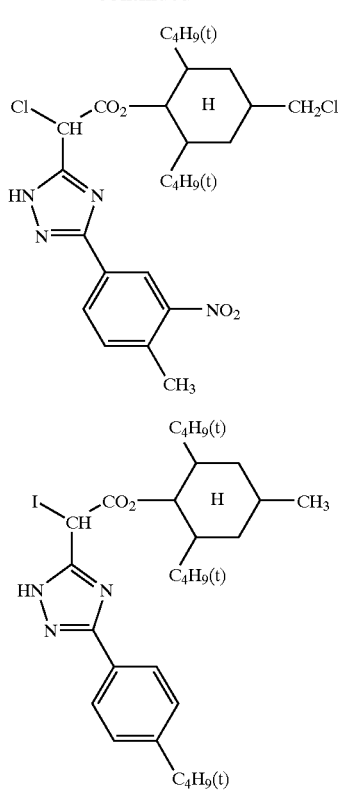

In the present invention, the reaction molar ratio of the cyclohexanols represented by formula (VI) to the carboxylic acids represented by formula (VII) follows the stoichiometric amounts, and it is preferably 10:1 to 1:1, and more preferably 3:1 to 1:1.

The reaction in the method of the present invention is preferably carried out in the presence of a base. The base may be either an organic base or an inorganic base.

As the organic base, guanidines (e.g. tetramethylguanidine and diphenylguanidine), trialkylamines (e.g. triethylamine, ethyldiisopropylamine, tributylamine, 1,8-diazabicyclo[5.4.0]-7-undecene (DBU), hexamethyltetramine, quinuclidine, 4-ethylmorpholine, and N-methylpiperidine), aliphatic polyamines (e.g. tetramethylethylenediamine and tetraethylethylenediamine), aromatic amines (e.g. dimethylaniline and dimethylaniline), and heterocyclic amines (e.g. pyridine, 2-picoline, 2-ethylpyridine, 3-picoline, 2,6-lutidine, pyridazine, pyrimidine, triazine, pyrazine, quinoline, isoquinoline, pyrrole, pyrazole, imidazole, 1,2,3-triazole, 1,2,4-triazole, tetrazole, indole, and benzotriazole) can be used. Preferably, trialkylamines, aromatic amines, and heterocyclic amines are used; more preferably trialkylamines and heterocyclic amines are used, and further more preferably trialkylamines are used.

Atoms other than hydrogen atoms and carbon atoms constituting these heterocyclic rings are oxygen, nitrogen, and sulfur atoms. The ring may be either a monocyclic ring or a condensed ring, with preference given to a monocyclic ring. The number of members of the ring is preferably 5 or 6.

As the inorganic base, for example, sodium formate, lithium oxalate, lithium hydroxide, sodium hydroxide, potassium hydroxide, lithium carbonate, sodium carbonate, potassium carbonate, lithium acetate, sodium acetate, potassium acetate, sodium monochloroacetate, potassium benzoate, sodium benzoate, sodium hydrogencarbonate, and potassium hydrogencarbonate can be used. Preferably sodium carbonate, potassium carbonate, sodium acetate, and potassium acetate are used, and more preferably potassium carbonate and potassium acetate are used.

The amount of the base to be used is suitably generally 0.1 to 10 mol equivalents, preferably 0.5 to 5.0 mol equivalents, and more preferably 1.0 to 3.0 mol equivalents, for the compound of formula (VI).

The amount of the carboxylic acid anhydride represented by formula (VIII) to be used is suitably generally 0.5 to 20 mol equivalents, preferably 2 to 10 mol equivalents, and more preferably 3 to 6 mol equivalents, per mol of the compound of formula (VI).

When the carboxylic acid anhydride represented by formula (VIII) is acetic anhydride, the amount of the acid or alkali to be used as a deacetylating agent is suitably generally 1 to 20 mol equivalents, preferably 2 to 10 mol equivalents, and more preferably 4 to 7 mol equivalents, per mol of the compound of formula (VI).

As the solvent, such a solvent as methylene chloride, 1,2-dichloroethane, chloroform, benzene, toluene, ethyl acetate, acetonitrile, nitromethane, tetrahydrofuran, diethyl ether, and diglyme can be used, with preference given to benzene, toluene, ethyl acetate, and acetonitrile, more preference given to ethyl acetate, acetonitrile, and toluene, and further preference given to ethyl acetate and toluene. The amount of the solvent to be used is suitably generally 2 to 50 times, and preferably 3 to 10 times, the weight amount of the compound of formula (VI).

The reaction temperature is generally −40 to 80° C., and preferably 20 to 60° C.

The reaction time is generally 0.1 to 10 hours, and preferably 1 to 5 hours.

To add the reagents, in the case using a base, there are a method in which the base is added to a solution of the cyclohexanols (VI) and the carboxylic acids (VII), and then the carboxylic acid anhydrides (VIII) is added, and a method in which the carboxylic acids (VII) are added to a solution of the cyclohexanols (VI) and the carboxylic acid anhydrides (VIII), and then the base is added, with preference given to the former method.

The 1H-pyrrole-[1,2-b][1,2,4]triazole compounds represented by formula (I) of the present invention are novel compounds, and they can be used in various applications. The 1H-pyrrole-[1,2-b][1,2,4]triazole compounds represented by formula (I) of the present invention are, for example, excellent in all of the following: as a photographic coupler, in storage stability, coupling activity, hue and fastness of the dye formed therefrom, prevention of stain during and after the processing, etc. Additionally stated, the compound represented by formula (I) can be synthesized from the compound represented by formula (III) without requiring an isolating step. This means that there is a considerable cost merit with regard to production.

Further, the 1H-1,2,4-triazole compounds represented by formula (II) or (III) of the present invention are useful as synthetic intermediates of the compounds represented by formula (I).

The compound represented by formula (I) of the present invention is excellent as a photographic cyan coupler. Particularly the cyan dye formed from this compound is excellent in hue, as well as in fastness to light.

Further, according to the method of the present invention, cyclohexyl=1H-1,2,4-triazole-5-yl-acetate compounds can be obtained, in a good yield, by condensing cyclohexanols with carboxylic acids with the use of a carboxylic acid anhydride under mild conditions.

The cyclohexyl 1H-1,2,4-triazole-5-yl-acetates obtained by the method of the present invention are useful as synthetic intermediates or their precursors of the 1H-pyrrole-[1,2]-b[1,2,4]triazole compounds represented by formula (I) of the present invention.

Hereinbelow, the present invention is described in more detail based on the following examples.

EXAMPLES

Example 1

Synthetic Example 1 Synthesis of Compounds (I)-(1), (II)-(1), and (III)-(1)

Compounds (I)-(1), (II)-(1), and (III)-(1) were synthesized in accordance with the following Scheme 1.

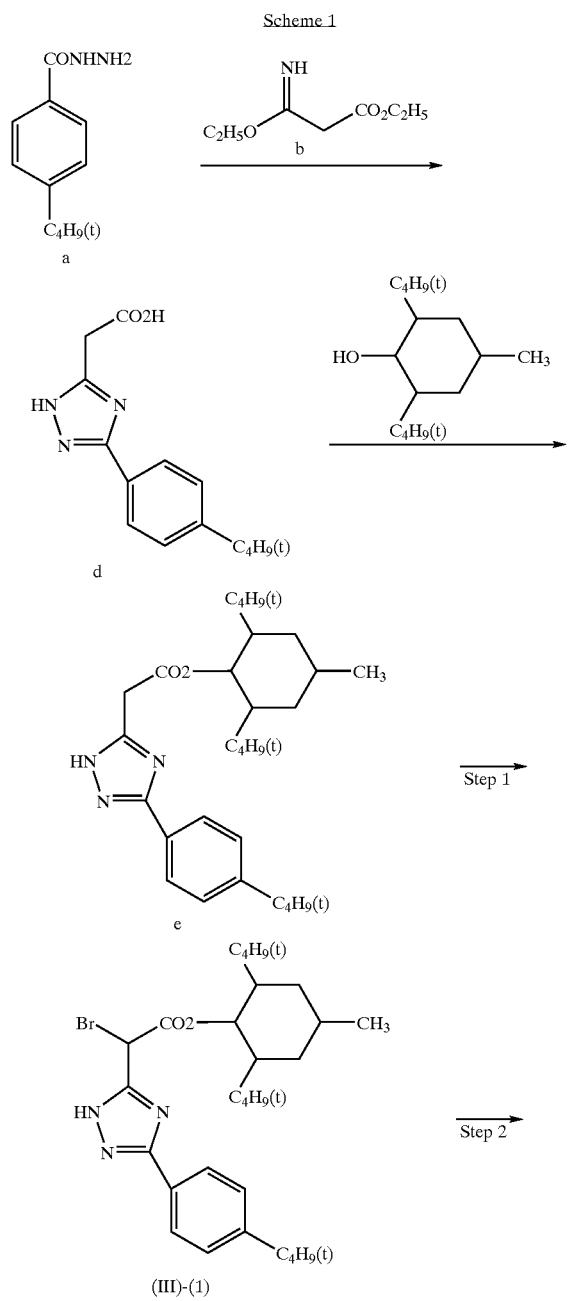

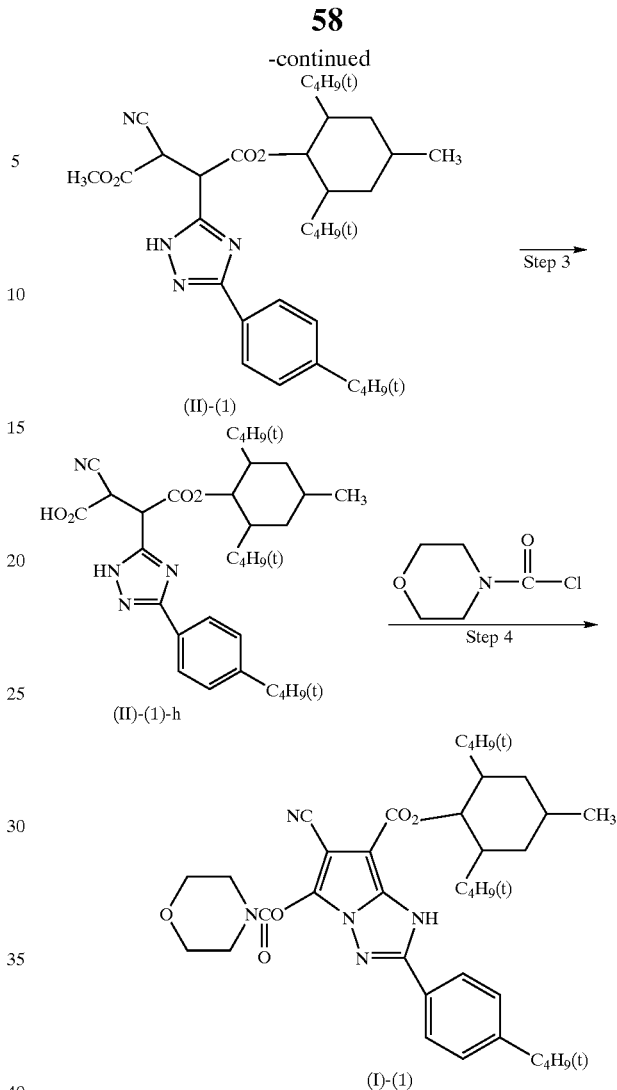

Synthesis of Compound d 20.5 g of sodium acetate was dissolved in 25 ml of methanol, and 38.4 g of p-t-butylbenzhydrazide (a) was added to the solution, with stirring. Thereafter, a solution of 41.4 g of the imidate (b) of ethyl cyanoacetate in 125 ml of methanol was added, dropwise, over 1 hour, with the internal temperature kept at 20° C. After reacting for 30 min, 53.0 g of sodium carbonate, in a powdery form, was added, and then 150 ml of warm water at 50° C. was added, dropwise, slowly, with the internal temperature kept at 50° C. Thereafter, the methanol was distilled off, with the internal temperature kept at 80° C. After the reaction, 200 ml of ethyl acetate was added at 35° C., and further, 86 ml of concentrated hydrochloric acid was added, for neutralization. After confirming that the pH of the aqueous phase was 4, the reaction liquid was cooled, for crystallization. The obtained crystals were filtered and dried, to obtain the desired Compound (d), in an amount of 42.4 g. The yield was 75.0%.

Synthesis of Compound e 182.3 ml of acetic anhydride was added, dropwise, to a solution of 100.0 g of Compound (d), 87.3 g of 2,6-di-t-butyl-4-methylcyclohexanol, and 5.3 g of potassium carbonate in 200 ml of toluene at room temperature. After the reaction, 300 ml of ethyl acetate was added, and then 99.3 ml of concentrated hydrochloric acid was added, slowly. Thereafter, the reaction mixture was stirred for 0.5 hr, with the internal temperature kept at 65° C. After the reaction, 300 ml of water was added, and then the layers were separated, followed by adding 30 ml of a 1-N aqueous sodium hydroxide solution, for extraction. The organic phase was condensed, and 120 ml of acetonitrile and 180 ml of toluene were added to the residue, for crystallization.

The obtained crystals were filtered and dried, to obtain Compound (e), in an amount of 156.7 g. The yield was 86.8%.

Synthesis of Compound (III)-(1)

100.0 g of Compound (e) was dissolved in 430 ml of ethyl acetate; then, 25.2 g of 2,6-lutidine was added, and 11.6 ml of bromine was added, dropwise, under cooling with ice. After the addition, the reaction was continued for 1 hour, and then 430 ml of water was added, to separate layers. After the organic layer was washed with water, the organic layer was condensed, and 645 ml of acetonitrile was added to the residue, for crystallization. The obtained crystals were filtered and 4 dried, to obtain Compound (III)-(1), in an amount of 107.4 g. The yield was 91.8%.

Synthesis of Exemplified Compound (I)-(1)

A 28% methanol solution containing 17.1 g of sodium methoxide was dissolved in 30 ml of dimethylacetamide, and then 8.1 ml of methyl cyanoacetate was added, at −10 to −5° C. Then, a solution of 20.0 g of Compound (III)-(1) in 30 ml of dimethylacetamide was added, dropwise, slowly, with the internal temperature kept at −10 to −5° C., to react them, to obtain Compound (II)-(1). Then, 8.5 g of potassium hydroxide dissolved in 15 ml of water, and 15 ml of methanol were added to the reaction liquid, and the reaction was continued for 1 hour, with the reaction temperature kept at about 60° C., to obtain Compound (II)-(1)-h. To the resulting reaction liquid, 100 ml of ethyl acetate, 50 ml of hexane, 14.6 ml of concentrated hydrochloric acid, and 100 ml of water were added; then, extraction was carried out, and the organic phase was washed with water twice and then was condensed. 40 ml of dimethylformamide and 15.0 ml of pyridine were added to the residue, and then 12.2 g of 4-morpholinocarbonylchloride was added, dropwise, with the internal temperature kept at 25° C. After reacting for 1 hour, 100 ml of methanol was added to the reaction liquid, and then 11.2 ml of concentrated hydrochloric acid and 10 ml of water were added, dropwise. After the addition, the reaction mixture was heated for 1 hour under reflux, and the crystals formed were filtered and dried, to obtain the intended Exemplified Compound (I)-(1), in an amount of 20.2 g. The yield based on Compound (III)-(1) was 84.7%. The melting point was 260° C.

Synthesis of Exemplified Compound (I)-(13)

A 28% methanol solution containing 8.6 g of sodium methoxide was dissolved in 15 ml of dimethylacetamide, and then 4.0 ml of methyl cyanoacetate was added, at −10 to −5° C. Then, a solution of 10.0 g of Compound (III)-(1) in 15 ml of dimethylacetamide was added, dropwise, slowly, with the internal temperature kept at −10 to −5° C., to react them, to obtain Compound (II)-(1). Then, 4.8 g of potassium hydroxide dissolved in 8 ml of water, and 8 ml of methanol were added to the reaction liquid, and the reaction was continued for 1 hour, with the reaction temperature kept at about 60° C., to obtain Compound (II)-(1)-h. To the resultant reaction liquid, 50 ml of ethyl acetate, 25 ml of hexane, 7.3 ml of concentrated hydrochloric acid, and 50 ml of water were added; then, extraction was carried out, and the organic phase was washed with water twice and then was condensed. 100 ml of pyridine was added to the residue, and then a solution of 4.5 g of dicyanoethylcarbonic acid chloride in 30 ml of methylene chloride was added, dropwise, with ice bath. After the reaction, 300 ml of ethyl acetate and 125 ml of concentrated hydrochloric acid were added, for neutralization, followed by washing with water twice. After the organic phase was condensed, the residue was purified by column chromatography and was recrystallized with acetonitrile. The crystals were filtered and dried, to obtain the intended Exemplified Compound (I)-(13), in an amount of 6.5 g. The yield was 54.7%. The melting point was 245 to 246° C.

Synthesis of Exemplified Compound (I)-(14)

A 28% methanol solution containing 23.6 g of sodium methoxide was dissolved in 40 ml of dimethylacetamide, and then 11.2 ml of methyl cyanoacetate was added, at −10 to −5° C. Then, a solution of 27.6 g of Compound (III)-(1) in 40 ml of dimethylacetamide was added, dropwise, slowly, with the internal temperature kept at −10 to −50° C., to react them, to obtain Compound (II)-(1). Then, 11.7 g of potassium hydroxide dissolved in 21 ml of water, and 20 ml of methanol were added to the reaction liquid, and the reaction was continued for 1 hour, with the reaction temperature kept at about 60° C., to obtain Compound (II)-(1)-h. To the resultant reaction liquid, 140 ml of ethyl acetate, 70 ml of hexane, 20 ml of concentrated hydrochloric acid, and 140 ml of water were added; and then, extraction was carried out, and the organic phase was washed with water twice and then was condensed. 100 ml of dimethylacetamide was added to the residue, and then 20.2 ml of pyridine was added, and then 15.9 g of diallylcarbonic acid chloride was added, dropwise. After the reaction, 300 ml of ethyl acetate and 125 ml of concentrated hydrochloric acid were added, for neutralization, followed by washing with water twice. After the organic phase was condensed, the residue was purified using column chromatography and was recrystallized with acetonitrile. The crystals were filtered and dried, to obtain the intended Exemplified Compound (I)-(14), in an amount of 20.5 g. The yield was 65.6%. The melting point was 217 to 218° C.

Synthesis of Exemplified Compound (I)-(15)

A 28% methanol solution containing 4.3 g of sodium methoxide was dissolved in 8 ml of dimethylacetamide, and then 2.0 ml of methyl cyanoacetate was added, at −10 to −5° C. Then, a solution of 5.0 g of Compound (III)-(1) in 8 ml of dimethylacetamide was added, dropwise, slowly, with the internal temperature kept at −10 to −5° C., to react them, to obtain Compound (II)-(1). Then, 2.4 g of potassium hydroxide dissolved in 4 ml of water, and 4 ml of methanol were added to the reaction liquid, and the reaction was continued for 1 hour, with the reaction temperature kept at about 60° C., to obtain Compound (II)-(1)-h. To the resultant reaction liquid, 25 ml of ethyl acetate, 12 ml of hexane, 3.7 ml of concentrated hydrochloric acid, and 25 ml of water were added; and extraction was carried out, and the organic phase was washed with water twice and then was condensed. 30 ml of pyridine was added to the residue, and then 2.0 g of dimethylcarbamoyl acid chloride was added, dropwise, on an ice bath. After the reaction, 100 ml of ethyl acetate and 38 ml of concentrated hydrochloric acid were added, for neutralization, followed by washing with water twice. After the organic phase was condensed, to the residue, was added acetonitrile, to carry out recrystallization from the acetonitrile. The crystals were filtered and dried, to obtain the intended Exemplified Compound (I)-(15), in an amount of 2.5 g. The yield was 45.7%. The melting point was 240 to 241° C.

Synthesis of Exemolified Compound (I)-(18)

A 28% methanol solution containing 4.3 g of sodium methoxide was dissolved in 8 ml of dimethylacetamide, and then 2.0 ml of methyl cyanoacetate was added, at −10 to −5° C. Then, a solution of 5.0 g of Compound (III)-(1) in 8 ml of dimethylacetamide was added, dropwise, slowly, with the internal temperature kept at −10 to −5° C., to react them, to obtain Compound (II)-(1). Then, 2.4 g of potassium hydroxide dissolved in 4 ml of water, and 4 ml of methanol were added to the reaction liquid, and the reaction was continued for 1 hour, with the reaction temperature kept at about 60° C., to obtain Compound (II)-(1)-h. To the resultant reaction liquid, 25 ml of ethyl acetate, 12 ml of hexane, 3.7 ml of concentrated hydrochloric acid, and 25 ml of water were added; then extraction was carried out, and the organic phase was washed with water twice and then was condensed. 30 ml of dimethylacetamide and 10 ml of pyridine were added to the residue, and then 3.1 g of 2-methylbenzoyl chloride was added, dropwise. After the reaction, 100 ml of ethyl acetate and 12 ml of concentrated hydrochloric acid were added, for neutralization, followed by washing with water twice. After the organic phase was condensed, the residue was purified by column chromatography and was recrystallized with acetonitrile. The crystals were filtered and dried, to obtain the intended Exemplified Compound (I)-(18), in an amount of 3.2 g. The yield was 54.2%. The melting point was 210 to 211° C.

Synthesis of Exemplified Compound (I)-(19)

A 28% methanol solution containing 17.1 g of sodium methoxide was dissolved in 30 ml of dimethylacetamide, and then 8.1 ml of methyl cyanoacetate was added, at −10 to −5° C. Then, a solution of 20.0 g of Compound (III)-(1) in 30 ml of dimethylacetamide was added, dropwise, slowly, with the internal temperature kept at −10 to −5° C., to react them, to obtain Compound (II)-(1). Then, 8.5 g of potassium hydroxide dissolved in 15 ml of water, and 15 ml of methanol were added to the reaction liquid, and the reaction was continued for 1 hour, with the reaction temperature kept at about 60° C., to obtain Compound (II)-(1)-h. To the resultant reaction liquid, 100 ml of ethyl acetate, 50 ml of hexane, 14.6 ml of concentrated hydrochloric acid, and 100 ml of water were added; then extraction was carried out, and the organic phase was washed with water twice and then was condensed. 60 ml of dimethylacetamide and 14.8 ml of pyridine were added to the residue, and then 13.7 g of 2-methoxybenzoyl chloride was added. After the reaction, 200 ml of ethyl acetate and 11 ml of concentrated hydrochloric acid were added, for neutralization, followed by washing with water twice. After the organic phase was condensed, the residue was purified on column chromatography and was recrystallized from acetonitrile. The crystals were filtered and dried, to obtain the intended Exemplified Compound (I)-(19), in an amount of 10.3 g. The yield was 42.6%. The melting point was 225 to 226° C.

Other compounds can also be synthesized in the similar manner as in the above-shown synthetic methods.

Reference Example

Using an undercoated polyethylene terephthalate base (support), a single-layered light-sensitive material Sample 101 having the below-shown layer structure for evaluation was prepared.

(Preparation of a Light-Sensitive Emulsion Layer Coating Solution)

1.85 mmol of a coupler was dissolved in 10 ml of ethyl acetate, dibutyl phthalate (solvent), in an added amount of 100% by weight based on the coupler, and tricresyl phosphate (solvent), in an added amount of 100% by weight based on the coupler. The resulting solution was emulsified and dispersed in 33 g of a 14% aqueous gelatin solution containing 3 ml of 10% sodium dodecylbenzenesulfonate. On the other hand, a silver chlorobromide emulsion (cubes of a 3:7 mixture (in terms of the molar ratio of silver) of a large-size emulsion, having an average grain size of 0.65 $\mu$m, and a small-size emulsion, having an average grain size of 0.55 $\mu$m, whose coefficient of variation of grain size distribution is 0.08 or 0.10, respectively, with each emulsion containing 0.3 mol % of silver bromide locally on part of the surface of the silver chloride grains), was prepared. Chemical ripening of the emulsion was carried out by adding a sulfur sensitizer and a gold sensitizer. The above emulsified dispersion and the emulsion were mixed and dissolved, to prepare a coating liquid for a light-sensitive emulsion layer, so that the coating solution would have the below-shown composition. In passing, as a hardener, 1-oxy-3,5-dichloro-s-triazine acid sodium salt was used.

(Layer Structure)

Hereinbelow, the layer structure of the sample used in this experiment is shown. (The figures are coated amounts per m².)

[Support]
Polyethylene terephthalate support
[Light-Sensitive Emulsion layer]

| | |
|---|---|
| Silver bromochloride emulsion (shown above) | 3.0 mmol |
| Coupler (shown in Table 1) | 1.0 mmol |
| Dibutyl phthalate | (100 wt % to the coupler) |
| Tricresyl phosphate | (100 wt % to the coupler) |
| Gelatin | 5.5 g |

[Protective layer]

| | |
|---|---|
| Gelatin | 2.5 g |
| Acryl-modified copolymer of polyvinyl alcohol (modification degree: 17%) | 0.15 g |
| Liquid paraffin | 0.03 g |

Structures of couplers for comparison used in this example and couplers of the present invention are shown below.

(Couplers for comparison)

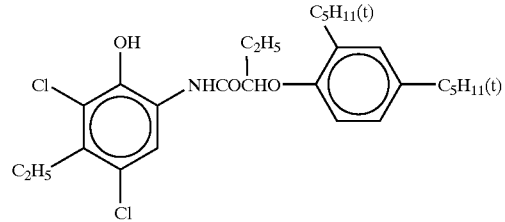

Ex-1

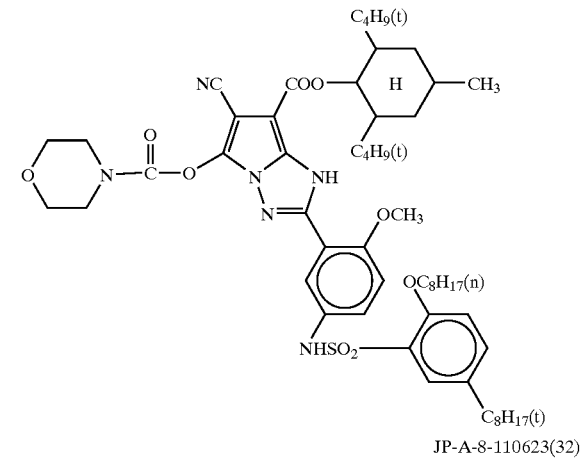

Ex-2

JP-A-8-110623(32)

-continued

Ex-3

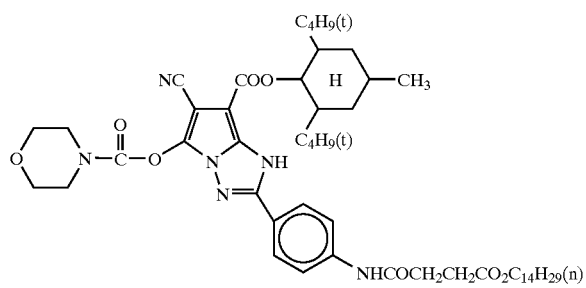

JP-A-8-110623(39)

Ex-4

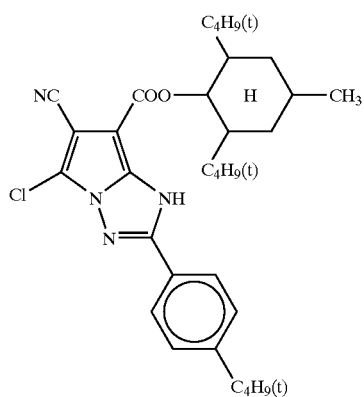

Samples 102 to 108 were prepared in the same manner as in the thus-prepared Sample 101, except that the cyan coupler and the high-boiling organic solvent were changed to the cyan coupler and the high-boiling organic solvent shown in Table 1. Herein, couplers were replaced in an amount of ½ in a molar amount, and an amount of silver halide was also changed to be ½. The thus-prepared samples were subjected to gradation exposure using an optical wedge, and then they were processed according to the following processing steps using the following processing solutions.

| (Processing steps) | | |
|---|---|---|
| Processing step | Temperature | Time |
| Color-development | 35° C. | 40 sec |
| Bleach-fixing | 35° C. | 40 sec |
| Washing | 35° C. | 90 sec |

| (Compositions of processing solutions) | |
|---|---|
| [Color-developer] | |
| Distilled water | 800 ml |
| Triethanolamine | 8.1 g |
| Diethylhydroxylamine | 4.2 g |
| Potassium bromide | 0.05 g |
| Sodium chloride | 0.5 g |

| -continued | |
|---|---|
| (Compositions of processing solutions) | |
| Sodium hydrogencarbonate | 3.9 g |
| Sodium sulfite | 0.13 g |
| N-ethyl-N-(β-methanesulfonamidoethyl)-3-methyl-4-aminoaniline sulfate | 5.0 g |
| Potassium carbonate | 18.7 g |
| Water to make | 1000 ml |
| pH | 10.15 |
| [Bleach-fixing solution] | |
| Distilled water | 400 ml |
| Ammonium thiosulfate (700 g/l) | 150 ml |
| Sodium sulfate | 18.0 g |
| Ethylenediaminetetraacetic acid Iron(III) ammonium salt | 55.0 g |
| Ethylenediaminetetraacetic acid | 5.0 g |
| Water to make | 1000 ml |
| pH | 6.70 |

The red light optical density of each of the processed samples was measured, to find the maximum color density $D_{max}$. The yellow density that gave a cyan density of 1.0 was measured by an X-Rite 310 densitometer (manufactured by X-Rite Company). It is shown that the lower the yellow density is, the lower the subsidiary absorption is, and the more excellent the hue is. Then, these samples were subjected to exposure to light for 5 days through a sharp cut filter that could cut about 50% at 380 nm, under a Xe light source of 200,000 lux (5-hour light/1-hour dark intermittent illumination) After the exposure to light, the red light optical density of each of the samples was again measured, to find the residual rate (survival rate) of the dye image after the exposure to light.

The dye image residual rate was evaluated at two points, including the $D_{max}$ part and a low-density part, where the color density was ⅕ of the $D_{max}$, and the rate was given in terms of percentage assuming the initial density to be 100%. The results are shown in Table 1.

TABLE 1

| Sample No. | Coupler | Hue (Y/C) | Residual Ratio of Dye Image $D_{max}$ | ⅕ $D_{max}$ | Remarks |
|---|---|---|---|---|---|
| 101 | Ex-1 | 0.250 | 88 | 84 | Comparative example |
| 102 | Ex-2 | 0.173 | 86 | 66 | " |
| 103 | Ex-3 | 0.172 | 85 | 65 | " |
| 104 | Ex-4 | 0.175 | 90 | 62 | " |
| 105 | I-1 | 0.175 | 90 | 82 | This invention |
| 106 | I-13 | 0.175 | 88 | 80 | " |
| 107 | I-14 | 0.175 | 90 | 81 | " |
| 108 | I-18 | 0.175 | 89 | 80 | " |

As is apparent from the results shown in Table 1, in comparison to Sample 101, Samples 102 to 108 are excellent in hue. However, Samples 102 to 104 are extremely poor in fastness to light in the low-density part and are apparently inferior to Comparative Sample 101. On the other hand, it can be understood that Samples 105 to 108, wherein the couplers according to the present invention are used, are not only excellent in hue but also remarkably improved in fastness to light in the low-density part, with the fastness to light hardly changed in the residual ratio from that of the high-density part. Thus, it can be said that the couplers according to the present invention are apparently excellent in hue and fastness to light.

Example 2

Esterification Reaction

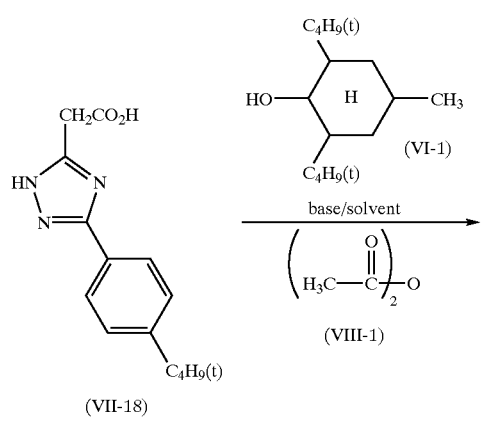

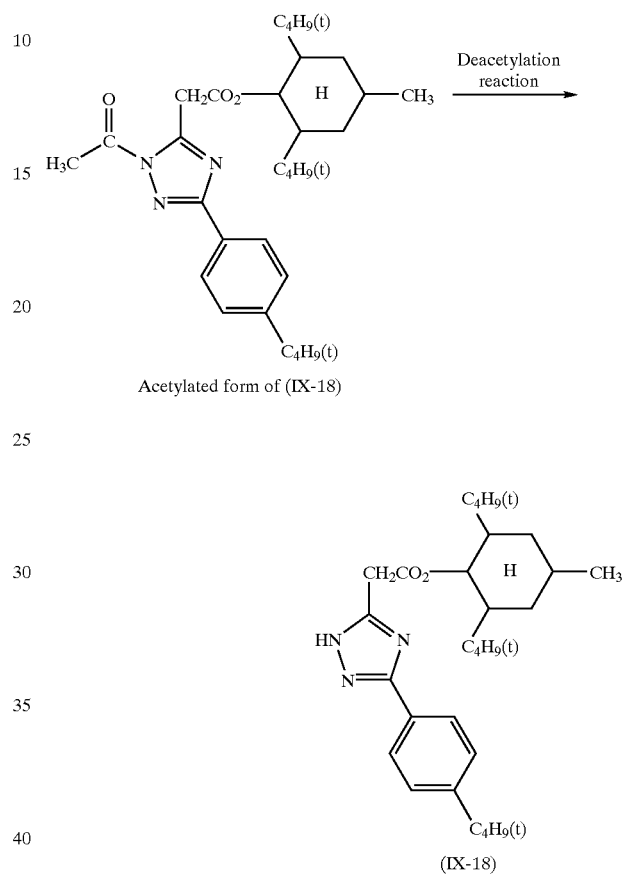

Compound (VII-18) (25.9 g, 0.10 mol) and a base were suspended in 100 ml of a solvent, and then Compound (VI-1) (22.6 g, 0.10 mol) was added, at 25° C. Then, Compound (VIII-1) (51.0 g, 0.50 mol) was added, dropwise, over 30 min. (The reaction temperature and the reaction time are given in the below table.) After the completion of the reaction was confirmed by thin-layer chromatography, water and ethyl acetate were added, and the layers were separated. The organic layer was dried, and after the solvent was distilled off, acetonitrile was added, to crystallize, to give Compound (IX-18) in an acetyl form. Their yields are shown in the below table. In passing, the structures were identified by NMR, IR, and mass spectrometry.

| Base | Reaction solvent and yield, reaction conditions | | |
|---|---|---|---|
| (equivalent) | Toluene % | Etyl acetate % | Acetonitril % |
| none | 78 (50° C., 3 hr) | 75 (50° C., 3 hr) | 74 (50° C., 3 hr) |
| K$_2$CO$_3$ (1) | 91 (40° C., 3 hr) | 86 (40° C., 3 hr) | 78 (40° C., 3 hr) |
| K$_2$CO$_3$ (2) | 92 (40° C., 3 hr) | 90 (40° C., 3 hr) | 79 (40° C., 3 hr) |
| Pyridine (3) | 88 (30° C., 2 hr) | 82 (30° C., 2 hr) | 83 (30° C., 2 hr) |
| Et$_3$N (3) | 90 (30° C., 2 hr) | 85 (30° C., 2 hr) | 84 (30° C., 2 hr) |

Example 3

Deacetylation Reaction

Compound (IX-18) in an acetyl form obtained in Example 2 was subjected to deacetylation reaction.

The acetylated form of Compound (IX-18) obtained in Example 2 (51.0 g, 0.10 mol) was dissolved in 100 ml of ethyl acetate, and then deacetylation agent was added, at 25° C. (The reaction temperature and the reaction time are given in the below table.) After the completion of the reaction was confirmed by thin-layer chromatography, water and ethyl acetate were added, and the layers were separated. The organic layer was dried, and after the solvent was distilled off, acetonitrile was added thereto, to crystallize, to give Compound (IX-18). Their yields are shown in the below table. In passing, the structures were identified by NMR, IR, and mass spectrometry.

| Deacetylation agent (equivalent) | Yield (%) and reaction conditions |
|---|---|
| NH$_4$OH (5) | 93 (60° C., 1 hr) |
| NaOCH$_3$ (5) | 90 (60° C., 1 hr) |
| HCl (5) | 95 (60° C., 1 hr) |

The above Examples 2 and 3 can be carried out sequentially. Some instances are given in Examples 4 to 14.

Example 4

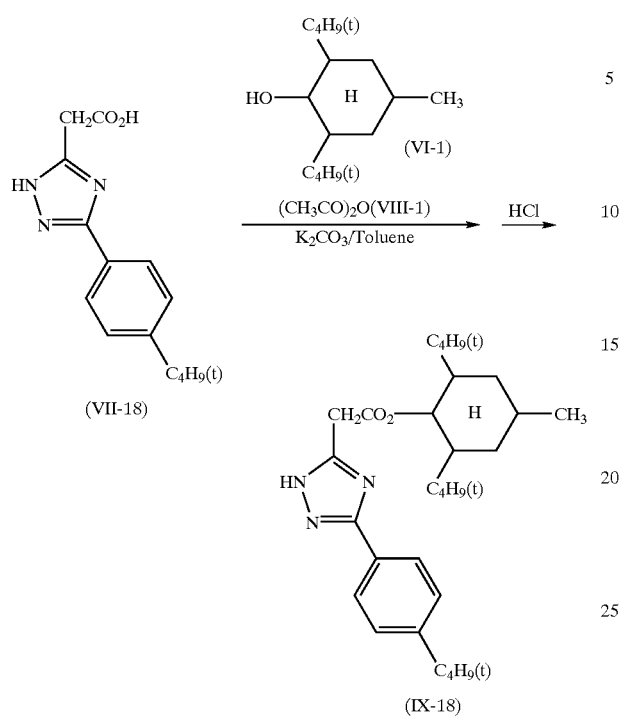

Compound (VII-18) (13.0 g, 0.05 mol) and potassium carbonate (6.9 g, 0.05 mol) were suspended in 50 ml of toluene, and then Compound (VI-1) (11.3 g, 0.05 mol) was added, at 25° C. Further, Compound (VIII-1) (25.5 g, 0.25 mol) was added, dropwise, over 30 min. The reaction was carried out for 5 hours with the internal temperature kept at 40° C., and the completion of the reaction was confirmed by thin-layer chromatography. Then, concentrated hydrochloric acid (21.5 ml, 0.25 mol) was added. The reaction was effected at 60° C. for 1 hour, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-18) (20.6 g, 0.044 mol), in a yield of 88%.

Example 5

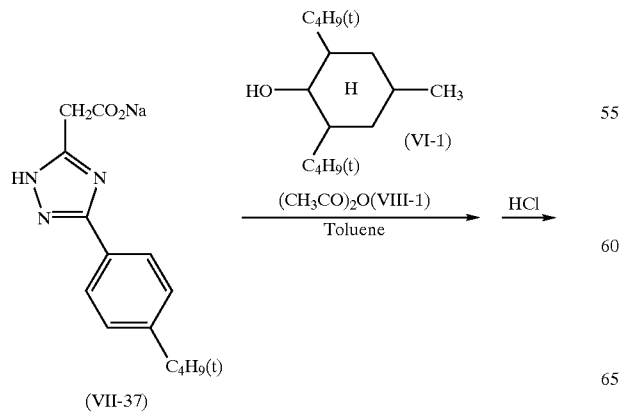

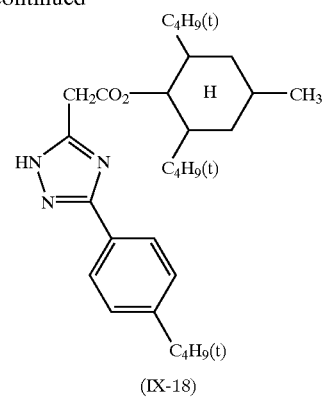

Compound (VII-37) (14.1 g, 0.05 mol) was suspended in 50 ml of toluene, and then Compound (VI-1) (11.3 g, 0.05 mol) was added at 25° C. Further, Compound (VIII-1) (25.5 g, 0.25 mol) was added, dropwise, over 30 min. The reaction was carried out at an internal temperature of 50° C. for 5 hours, and the completion of the reaction was confirmed by thin-layer chromatography. Then, concentrated hydrochloric acid (25.7 ml, 0.30 mol) was added. The reaction was carried out at 60° C. for 1 hour, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-18) (20.1 g, 0.043 mol), in a yield of 86%.

Example 6

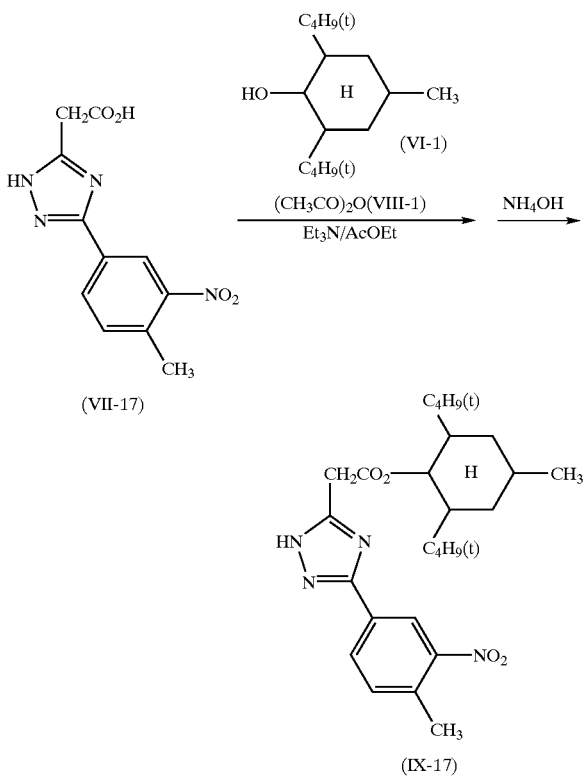

Compound (VII-17) (7.9 g, 0.03 mol) and triethylamine (9.1 g, 0.09 mol) were suspended in 30 ml of ethyl acetate, and then Compound (VI-1) (6.8 g, 0.03 mol) was added at 25° C. Further, Compound (VIII-1) (15.3 g, 0.15 mol) was added, dropwise, over 30 min. The reaction was carried out at an internal temperature of 30° C. for 3 hours, and the completion of the reaction was confirmed by thin-layer chromatography. Then, aqueous ammonia (29%, 9.8 ml, 0.15 mol) was added. The reaction was carried out at 60° C. for 1 hour, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-17) (11.6 g, 0.025 mol), in a yield of 82%. In passing, the structures were identified by NMR, IR, and mass spectrometry.

Example 7

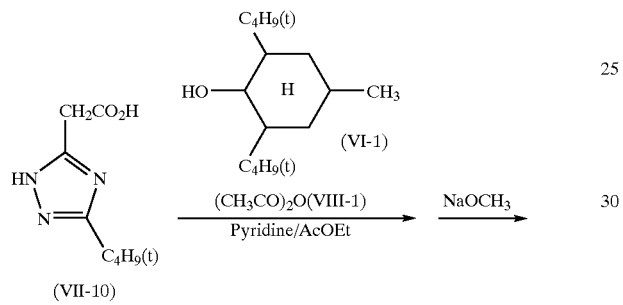

(VII-10)

(IX-10)

Compound (VII-10) (4.6 g, 0.025 mol) and pyridine (5.9 g, 0.075 mol) were dissolved in 30 ml of ethyl acetate, and then Compound (VI-1) (5.7 g, 0.025 mol) was added at 25° C. Further, Compound (VIII-1) (12.8 g, 0.125 mol) was added, dropwise, over 30 min. The reaction was carried out at an internal temperature of 30° C. for 3 hours, and the completion of the reaction was confirmed by thin-layer chromatography. Then, sodium methylate (28%, 30.8 ml, 0.15 mol) was added. The reaction was carried out at 60° C. for 1 hour, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-10) (7.8 g, 0.02 mol), in a yield of 85%. In passing, the structures were identified by NMR, IR, and mass spectrometry.

Example 8

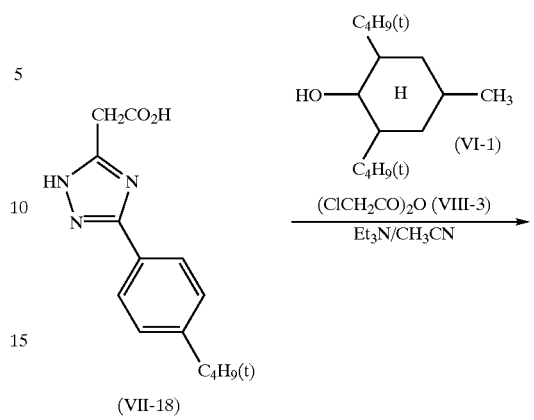

(VII-18)

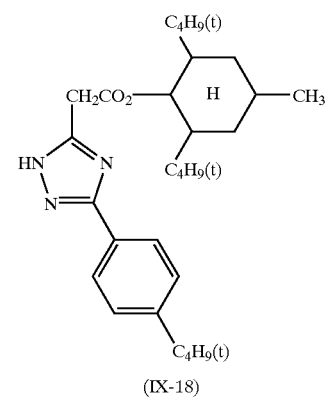

(IX-18)

Compound (VII-18) (13.0 g, 0.05 mol) and triethylamine (10.1 g, 0.10 mol) were suspended in 50 ml of acetonitrile, and then Compound (VI-1) (11.3 g, 0.05 mol) was added at 25° C. Further, Compound (VIII-3) (27.0 g, 0.25 mol) was added, dropwise, over 30 min. The reaction was carried out at an internal temperature of 30° C. for 5 hours, and the completion of the reaction was confirmed by thin-layer chromatography. Then, concentrated hydrochloric acid (21.5 ml, 0.25 mol) was added. The reaction was carried out at 60° C. for 1 hour, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-18) (19.2 g, 0.041 mol), in a yield of 82%.

Example 9

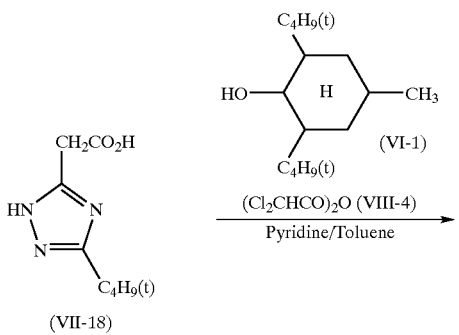

(VII-18)

-continued

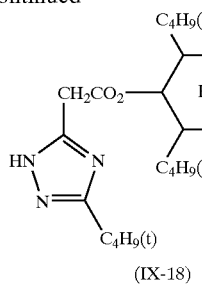

(IX-18)

Compound (VII-10) (5.5 g, 0.03 mol) and pyridine (4.7 g, 0.06 mol) were suspended in 30 ml of ethyl acetate, and then Compound (VI-1) (6.8 g, 0.03 mol) was added at 25° C. Further, Compound (VIII-4) (43.1 g, 0.18 mol) was added, dropwise, over 30 min. The reaction was carried out at an internal temperature of 40° C. for 3 hours, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-10) (8.8 g, 0.023 mol), in a yield of 75%.

Example 10

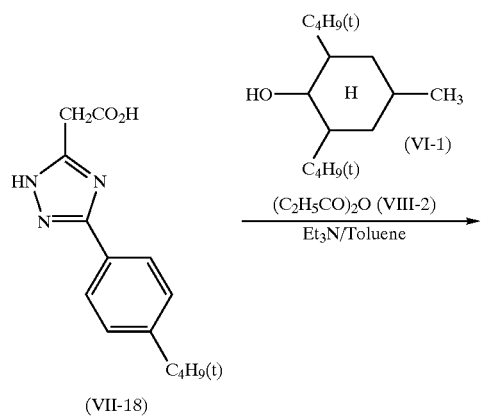

Compound (VII-18) (6.5 g, 0.025 mol) and triethylamine (7.6 g, 0.075 mol) were suspended in 30 ml of toluene, and then Compound (VI-1) (5.7 g, 0.025 mol) was added at 25° C. Further, Compound (VIII-2) (16.3 g, 0.125 mol) was added, dropwise, over 30 min. The reaction was carried out at an internal temperature of 30° C. for 2 hours, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-18) (9.4 g, 0.02 mol), in a yield of 85%.

Example 11

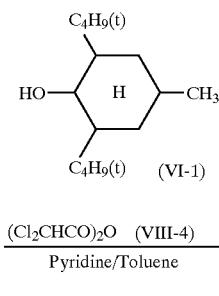

(VII-18)

$(Cl_2CHCO)_2O$ (VIII-4)
Pyridine/Toluene
→

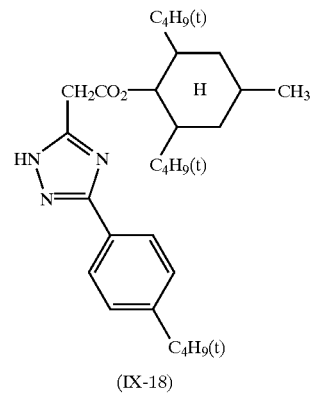

(IX-18)

Compound (VII-18) (7.8 g, 0.03 mol) and pyridine (7.1 g, 0.09 mol) were suspended in 30 ml of toluene, and then Compound (VI-1) (6.8 g, 0.03 mol) was added at 25° C. Further, Compound (VIII-4) (36.0 g, 0.15 mol) was added, dropwise, over 30 min. The reaction was carried out at an internal temperature of 30° C. for 3 hours, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-18) (10.7 g, 0.023 mol), in a yield of 76%.

Example 12

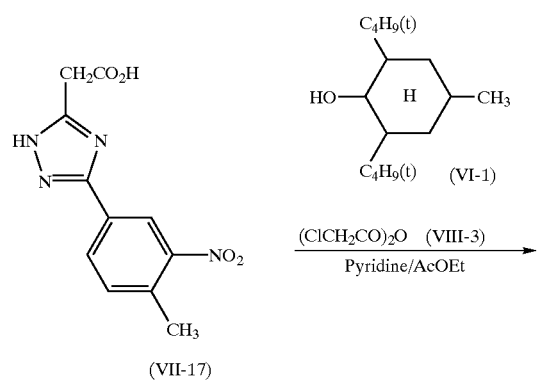

Compound (VII-17) (6.6 g, 0.025 mol) and pyridine (5.9 g, 0.075 mol) were dissolved in 30 ml of ethyl acetate, and then Compound (VI-1) (5.7 g, 0.025 mol) was added at 25° C. Further, Compound (VIII-3) (21.4 g, 0.125 mol) was added, dropwise, over 30 min. The reaction was carried out at an internal temperature of 40° C. for 2 hours, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-17) (9.3 g, 0.02 mol), in a yield of 79%.

Example 13

(VII-1) +

Example 14

(VII-17)

Compound (VII-1) (6.2 g, 0.025 mol) and potassium carbonate (10.4 g, 0.075 mol) were suspended in 30 ml of ethyl acetate, and then Compound (VI-37) (11.8 g, 0.025 mol) was added at 25° C. Further, Compound (VIII-1) (12.8 g, 0.125 mol) was added, dropwise, over 30 min. The reaction was carried out at an internal temperature of 50° C. for 2 hours, and the completion of the reaction was confirmed by thin-layer chromatography. Then, concentrated hydrochloric acid (21.5 ml, 0.25 mol) was added. The reaction was carried out at 60° C. for 1 hour, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-36) (12.7 g, 0.018 mol), in a yield of 71%.

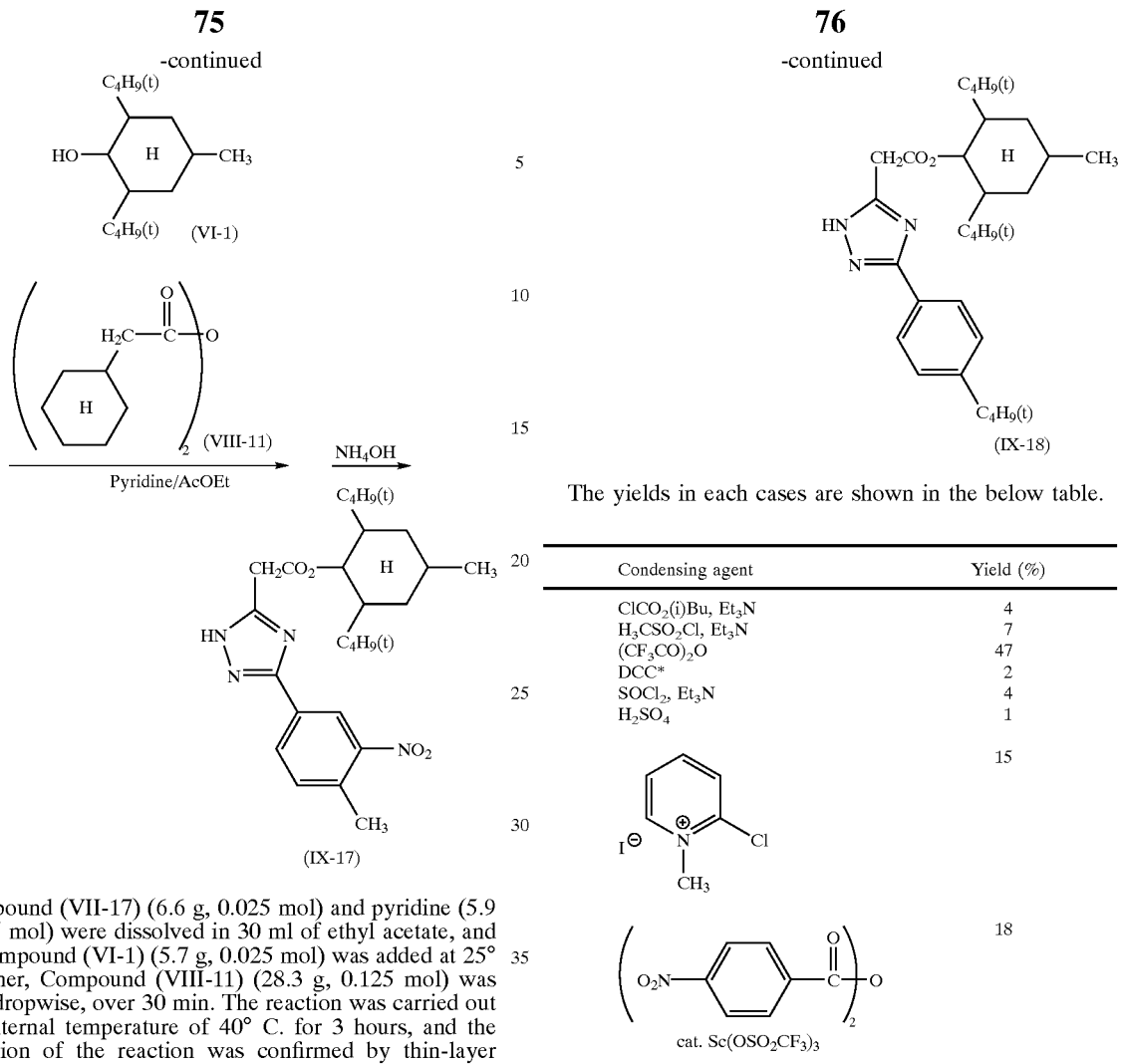

The yields in each cases are shown in the below table.

| Condensing agent | Yield (%) |
| --- | --- |
| ClCO$_2$(i)Bu, Et$_3$N | 4 |
| H$_3$CSO$_2$Cl, Et$_3$N | 7 |
| (CF$_3$CO)$_2$O | 47 |
| DCC* | 2 |
| SOCl$_2$, Et$_3$N | 4 |
| H$_2$SO$_4$ | 1 |
| (2-chloro-1-methylpyridinium iodide) | 15 |
| (bis(4-nitrobenzoyl) anhydride), cat. Sc(OSO$_2$CF$_3$)$_3$ | 18 |

*Dicyclohexylcarbodiimide

All of the conventional processes are quite low in yield, and it is apparent that they are not practical.

Example 15

As a use of the acetate compounds obtained by the method of the present invention, for example, they can be each led to a color coupler via steps shown in the following Scheme (ii). Hereinbelow, Compound IX-42 is described as an example.

Compound (VII-17) (6.6 g, 0.025 mol) and pyridine (5.9 g, 0.075 mol) were dissolved in 30 ml of ethyl acetate, and then Compound (VI-1) (5.7 g, 0.025 mol) was added at 25° C. Further, Compound (VIII-11) (28.3 g, 0.125 mol) was added, dropwise, over 30 min. The reaction was carried out at an internal temperature of 40° C. for 3 hours, and the completion of the reaction was confirmed by thin-layer chromatography. Then, aqueous ammonia (29%, 16.3 ml, 0.125 mol) was added. The reaction was carried out at 60° C. for 1 hour, and the completion of the reaction was confirmed by thin-layer chromatography. Thereafter, water and ethyl acetate were added, and the layers were separated. After the organic layer was dried and the solvent was distilled off, acetonitrile was added, to crystallize, to give Compound (IX-17) (8.9 g, 0.019 mol), in a yield of 76%.

Comparative Example

The synthesis of Compound (IX-18) was carried out with the use of the generally well-known esterification reaction of Compound (VII-18) and Compound (VI-1).

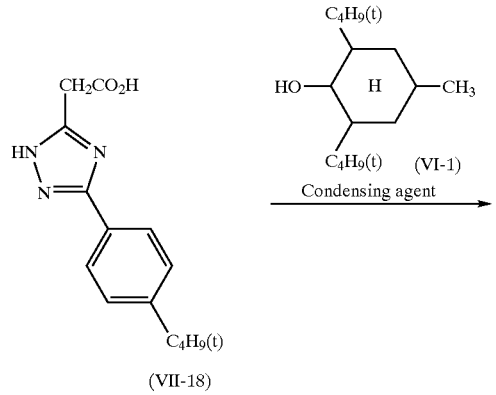

Scheme (ii)

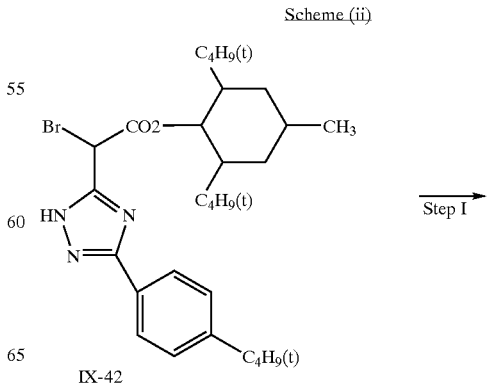

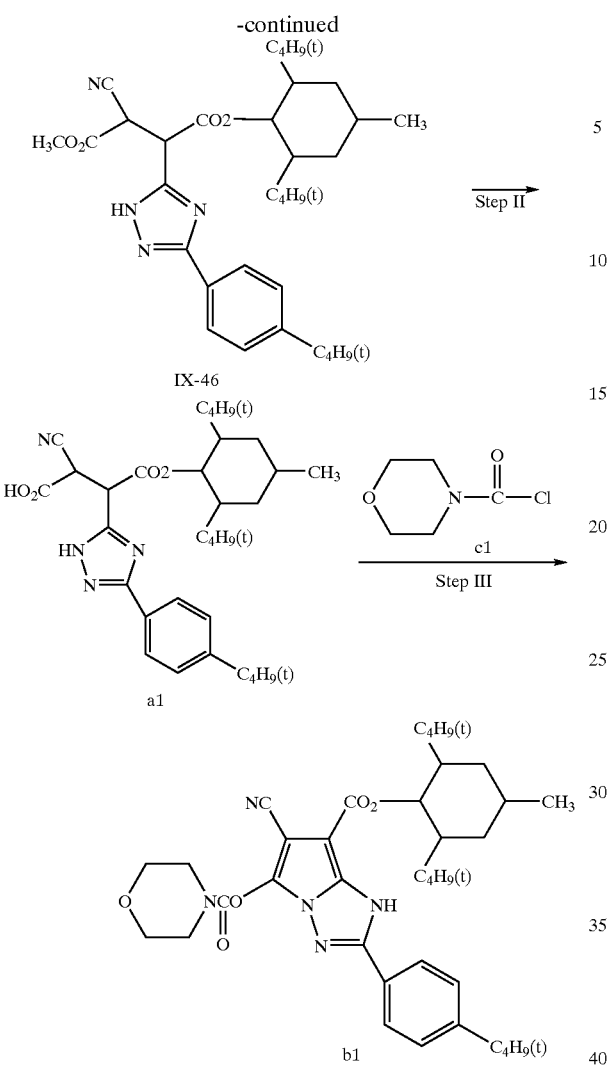

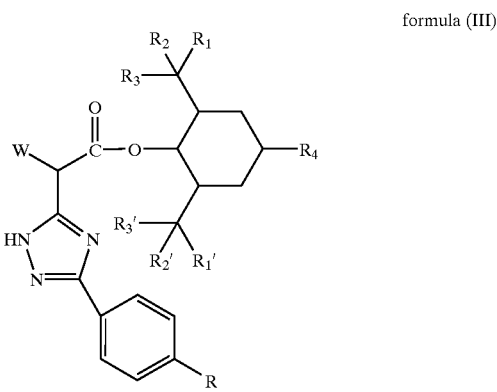

First, Compound IX-42 was reacted with cyanoacetates, to obtain Compound IX-46. Then, this Compound IX-46 was hydrolyzed, to obtain Compound (a1). This Compound (a1) was then reacted with Acid halide (c1), to obtain Compound (b1), which is useful as a color coupler.

Details on this process are described in the above Example 1.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A 1H-1,2,4-triazole compound represented by formula (III):

formula (III)

wherein, in formula (III), R represents a straight-chain or branched-chain alkyl group having 1 to 12 carbon atoms; $R_1$, $R_2$, $R_3$, $R_1'$, $R_2'$ and $R_3'$, which may be the same or different, each represent a hydrogen atom, a straight-chain or branched-chain alkyl group having 1 to 24 carbon atoms, or a cyclic alkyl group having 3 to 8 carbon atoms; $R_1$ and $R_2$, and $R_1'$ and $R_2'$, may bond together to form an alkylene group having 1 to 12 carbon atoms, respectively, $R_4$ represents a hydrogen atom, a straight-chain or branched-chain alkyl group having to 1 to 36 carbon atoms, or a cyclic alkyl group having 3 to 8 carbon atoms, and W represents a halogen atom.

2. The 1H-1,2,4-triazole compound as claimed in claim 1, wherein R represents a t-butyl group.

3. The 1H-1,2,4-triazole compound as claimed in claim 1, wherein $R_1$, $R_2$, $R_3$, $R_1'$, $R_2'$ and $R_3'$ each represent a methyl group.

4. The 1H-1,2,4-triazole compound as claimed in claim 1, wherein $R_4$ represents a methyl group.

5. The 1H-1,2,4-triazole compound as claimed in claim 1, wherein W represents a bromine atom.

* * * * *